US010874759B2

(12) United States Patent
Ma et al.

(10) Patent No.: US 10,874,759 B2
(45) Date of Patent: Dec. 29, 2020

(54) STERILIZATION PROCESS MANAGEMENT

(71) Applicant: 3M INNOVATIVE PROPERTIES COMPANY, Saint Paul, MN (US)

(72) Inventors: Judy J. Ma, Woodbury, MN (US); G. Marco Bommarito, Stillwater, MN (US); Amelia Fish, Minneapolis, MN (US); Rothanak Chhoun, Apple Valley, MN (US); Christina M. Dimeo, Minneapolis, MN (US); Maneesh Shrivastav, Blaine, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 16/359,552

(22) Filed: Mar. 20, 2019

(65) Prior Publication Data
US 2019/0290796 A1    Sep. 26, 2019

Related U.S. Application Data

(60) Provisional application No. 62/645,426, filed on Mar. 20, 2018.

(51) Int. Cl.
*G06Q 30/00* (2012.01)
*A61L 2/24* (2006.01)
(52) U.S. Cl.
CPC .............. *A61L 2/24* (2013.01); *A61L 2202/14* (2013.01); *A61L 2202/24* (2013.01)
(58) Field of Classification Search
CPC ..... A61B 90/70; A61B 90/90; A61L 2202/14; A61L 2202/24; A61L 2/10; A61L 2/24; A61L 2/28; G06F 16/2379; G06K 2209/057; G06K 9/6253; G16H 20/40; G16H 40/20
See application file for complete search history.

(56) References Cited

U.S. PATENT DOCUMENTS

| 4,448,548 A | 5/1984 | Foley |
| 5,488,815 A | 2/1996 | Abrams |

(Continued)

FOREIGN PATENT DOCUMENTS

| DE | 102008021490 | 11/2009 |
| WO | WO 1994-015536 | 7/1994 |

(Continued)

OTHER PUBLICATIONS

Afridi, "Automatic in Vivo Cell Detection in MRI", A paper presented in International Conference on Medical Image Computing and Computer-Assisted Intervention, Oct. 2015, 8 pages.

(Continued)

*Primary Examiner* — Thien M Le
(74) *Attorney, Agent, or Firm* — Jonathan V. Sry; Sriram Srinivasan

(57) ABSTRACT

Aspects of the present disclosure relate to a system including an image capture device and a computing device configured to receive a test image from the image capture device corresponding to a first surgical instrument, determine an identity type of the first surgical instrument using the test image in a machine vision technique, determine whether the first surgical instrument is flagged, and perform at least one operation in response to whether the first surgical instrument is flagged.

21 Claims, 19 Drawing Sheets

(56) References Cited

U.S. PATENT DOCUMENTS

| | | | |
|---|---|---|---|
| 5,696,686 | A | 12/1997 | Sanka |
| 6,025,189 | A | 2/2000 | Bolea |
| 6,238,623 | B1 | 5/2001 | Amhof |
| 6,485,979 | B1 | 11/2002 | Kippenhan |
| 6,991,761 | B2 | 1/2006 | Hehenberger |
| 7,053,958 | B2 | 5/2006 | Collins |
| 7,422,334 | B2 | 9/2008 | Smith |
| 7,518,502 | B2 | 4/2009 | Austin |
| 7,617,137 | B2 | 11/2009 | Kreiner |
| 7,722,521 | B2 | 5/2010 | Heath |
| 7,734,476 | B2 | 6/2010 | Wildman |
| 7,818,182 | B2 | 10/2010 | Giraldo |
| 8,042,738 | B2 | 10/2011 | Cloix |
| 8,291,472 | B2 | 10/2012 | Bak |
| 9,305,218 | B2 | 4/2016 | Lewis |
| 2006/0153736 | A1 | 6/2006 | Kalra |
| 2007/0094303 | A1 | 4/2007 | Zwingenberger |
| 2008/0215366 | A1 | 9/2008 | Robson |
| 2009/0272806 | A1 | 11/2009 | Kemp |
| 2011/0246219 | A1 | 10/2011 | Smith |
| 2013/0034682 | A1 | 2/2013 | Free |
| 2013/0066647 | A1 | 3/2013 | Andrie |
| 2013/0114142 | A1 | 5/2013 | Free |
| 2014/0368902 | A1 | 12/2014 | Patel |
| 2015/0043074 | A1 | 2/2015 | Patel |
| 2015/0173843 | A1 | 6/2015 | Maughan |
| 2016/0042130 | A1 | 2/2016 | Broninx |
| 2016/0045276 | A1 | 2/2016 | Pfanner |
| 2016/0321825 | A1 | 11/2016 | Karasawa |
| 2017/0098049 | A1 | 4/2017 | Sweeney |
| 2017/0224438 | A1 | 8/2017 | Johnson |
| 2017/0348452 | A1 | 12/2017 | Kuzelka |
| 2018/0018642 | A1 | 1/2018 | Schmitz |
| 2019/0125458 | A1* | 5/2019 | Shelton, IV ......... A61B 17/105 |
| 2019/0200844 | A1* | 7/2019 | Shelton, IV ....... A61B 18/1445 |
| 2019/0201136 | A1* | 7/2019 | Shelton, IV ............ A61B 90/53 |
| 2019/0201143 | A1* | 7/2019 | Shelton, IV ............ H04W 4/38 |
| 2019/0206551 | A1* | 7/2019 | Yates ............... A61B 17/32009 |
| 2019/0206561 | A1* | 7/2019 | Shelton, IV ........... G16H 50/70 |
| 2019/0206565 | A1* | 7/2019 | Shelton, IV ........... A61B 34/74 |
| 2019/0206569 | A1* | 7/2019 | Shelton, IV ....... A61B 1/00016 |

FOREIGN PATENT DOCUMENTS

| | | |
|---|---|---|
| WO | WO 2007-000639 | 1/2007 |
| WO | WO 2010-018464 | 2/2010 |
| WO | WO 2015-192117 | 12/2015 |
| WO | WO 2017-103804 | 6/2017 |
| WO | WO 2017-117359 | 7/2017 |
| WO | WO 2017-173017 | 10/2017 |
| WO | WO 2018-064212 | 4/2018 |

OTHER PUBLICATIONS

Brownlee, "A Gentle Introduction to Transfer Learning for Deep Learning" Machine Learning Mastery Pty. Ltd. PO Box 206, Vermont Victoria 3133, Australia, [Published on internet on Dec. 20, 2017], [retrieved, from the internet on Apr. 4, 2019], URL <https://machinelearningmastery.com/transfer-learning-for-deep-learning/> 22 pages.

"Gaussian mixture models" Scikit-learn v0.20.3, [retrieved from the internet on Apr. 4, 2019], URL <https://scikit-learn.org/stable/modules/mixture.html> 9 pages.

Kurmann, "Simultaneous Recognition and Pose Estimation of Instruments in Minimally Invasive Surgery", A Paper presented in International Conference on Medical Image Computing and Computer-Assisted Intervention, Oct. 2017,8 pages.

Law, "Surgeon Technical Skill Assessment using Computer Vision Based Analysis", Proceedings of Machine Learning for Healthcare, 2017, JMLR W&C Track vol. 68, 12 pages.

Letouzey, "Instruments Localisation and Identification for Laparoscopic Surgeries", Computational Analysis and Modeling of Medical Activities, M2CAI Reports, 2016, 8 pages.

Mao, "Robotic Handling of Surgical Instruments in a Cluttered Tray", IEEE Transactions on Automation Science and Engineering, Apr. 2015, vol. 12, No. 2, pp. 775-780.

Murillo, "Comparison Between CNN and Haar Classifiers for Surgical Instrumentation Classification", Contemporary Engineering Sciences, 2017, vol. 10, No. 28, pp. 1351-1363.

Sternberg, "Biomedical Image Processing", IEEE Journals & Magazines, Jan. 1983, vol. 16, No. 1, pp. 22-34.

"Subtract background"[ImageJ Documentation Wiki], [retrieved from the internet on Mar. 28, 2018], URL <https://imagejdocu.tudor.lu/doku.php?id=gui:process:subtract_background> 2 pages.

Xu, "Robotic Handling of Surgical Instruments in a Cluttered Tray", IEEE Transactions on Automation Science and Engineering, Apr. 2015, vol. 12, No. 2, pp. 775-780.

* cited by examiner

STERILIZATION PROCESS MANAGEMENT

CROSS REFERENCE TO RELATED APPLICATIONS

This application claims priority from U.S. Provisional Application Ser. No. 62/645,426, filed Mar. 20, 2018, the disclosure of which is incorporated by reference in its entirety herein.

BACKGROUND

Surgical device reprocessing can be performed by the central sterile services department of a hospital. Further, surgical device reprocessing can be prone to failure due to inadequate tracking of complicated, complex processes. Any failure can result in a variety of issues for a hospital such as a cost in loss of productivity, mismanagement of equipment and materials, and even potential harm to patients through healthcare associated infection.

Collecting and analyzing data regarding surgical instruments and their movement throughout the hospitals (from Central Sterile to the Operating Room and back) is important, both for managing inventory and identifying location of the inventory, as well as identifying which instruments are used on which patients.

SUMMARY

While machine vision techniques have been used to identify individual surgical instruments, machine vision techniques may have difficulty large data sets where a large number of potential surgical instruments may require significant computing resources. Further, machine vision techniques may have issues with confidence values and lead to some questionable classifications. Further, various processes of sterilization management are not necessarily linked to a machine vision system.

Aspects of the present disclosure relate to a system including an image capture device and a computing device configured to receive a test image from the image capture device corresponding to a first surgical instrument, determine an identity type of the first surgical instrument using the test image in a machine vision technique, determine whether the first surgical instrument is flagged, and perform at least one operation in response to whether the first surgical instrument is flagged.

Aspects of the present disclosure also relate to a system including an image capture device, and an analytical device. A computing device can be communicatively coupled to the image capture device and the analytical device and configured to determine, based on a machine vision technique from the image capture device, that a wrapped package is assembled with a group of one or more surgical instruments, receive a sterilization status for the group from the analytical device, and perform at least one operation based on the sterilization status.

Aspects of the present disclosure also relate to a system including an image capture device, a surgical instrument, and a display. The computing device can be communicatively coupled to the image capture device and the display and be configured to receive a template for a plurality of surgical instruments, the template comprises an image describing position information for the plurality of surgical instruments, receive, from the image capture device, a video feed of the surgical instrument, determine an instrument type and position of the surgical instrument from the video feed, determine whether the type and position of the surgical instrument corresponds to a surgical instrument of the template, and perform at least one operation in response to the determination of the instrument type of the surgical instrument.

BRIEF DESCRIPTION OF DRAWINGS

FIG. 9 illustrates an image of a user interface featuring a template, according to various embodiments.

FIG. 10 illustrates an image of a user interface featuring a template with zoom capability, according to various embodiments.

FIG. 12 illustrates an image of a user interface featuring a template with a chemical indicator, according to various embodiments.

DETAILED DESCRIPTION

Aspects of the present invention can provide operations in response to flagged events and be useful in combining sterilization management with machine vision techniques.

Figure 1:
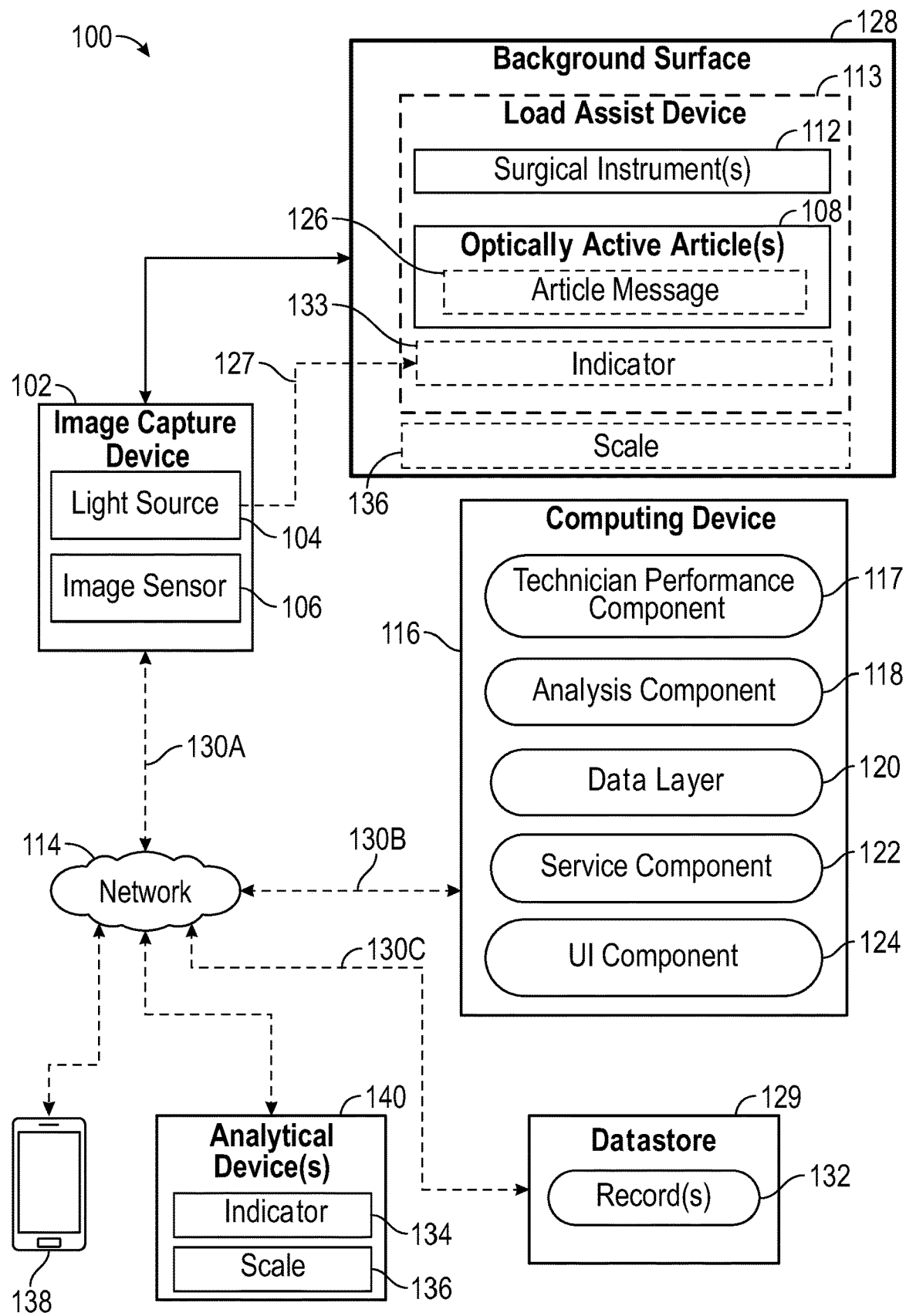
FIG. 1 illustrates a block diagram of a system for performing aspects of the present disclosure.

FIG. 1 is a block diagram illustrating an example system 100 for optically determining an identity type of a surgical instrument 112. As shown in FIG. 1, system 100 includes an image capture device 102. Image capture device 102 may include one or more image capture sensors 106 and one or more light sources 104.

The one or more surgical instruments 112 can be placed in a load assist device 113 (which can withstand a sterilization process). In at least one embodiment, the load assist device 113 can be a wheeled cart capable of receiving multiple surgical instruments 112. The load assist device 113 can also be a tray capable of receiving multiple surgical instruments 112. The load assist device 113 can be configured to be placed in a sterilizer. To facilitate recognizing the borders of the load assist device 113, one or more optically active articles can be placed around the perimeter of a load assist device 113 (e.g., around the top perimeter of a tray) The optically active article can include retroreflective, or reflective tape such that a vision-based system can recognize the border of the load assist device 113.

In at least one embodiment, a load assist device 113 or the surgical instrument 112 can be placed on a background surface 128. The background surface 128 is a surface that can facilitate determining an identity type of the surgical instrument 112. The background surface 128 can also be optically contrasting with the surgical instrument (e.g., a blue nonwoven for a stainless-steel instrument 112).

The background surface 128 can have markers embedded or printed thereon which facilitates scaling of the image. For example, hatch-marks or grids can be formed on the background surface to provide scale for the surgical instrument 112 and may be used to gauge the relative sizes of the instruments. In some embodiments, the scale can comprise a ruler that is found within the pack of instruments.

The background surface 128 can also include regions responsive to certain instrument types. For example, the background surface 128 can have a region for locking instruments, clamping instruments, a region for lumened instruments, etc. to facilitate identification of the instrument by the system 100. Such a regioned area can specifically facilitate supervised learning (as described herein. The background surface 128 can interface with the UI Component 120 to provide controls for the computing device 116. For example, the background surface 128 can have tactile buttons, projected interface buttons, gestural touch, etc.

In at least one embodiment, the background surface 128 can include a scale 136 to measure a mass of the surgical instrument. The mass of the surgical instrument can be identified as a feature and combined with the image analysis to aid in identifying the identity type of the surgical instrument. For example, if there is an 88% confidence that an image of a surgical instrument is an alligator forceps, and the mass measured indicates that the surgical instrument is approximately the same mass as alligator forceps, then the confidence can be increased, by the computing device 116.

Further, the background surface can also include markers which can further facilitate outlines of the surgical instruments. For example, a microreplicated surface in a rectilinear array to provide a greater number of reference points. The background surface 128 can be formed of any material such as a nonwoven and be relatively flat to provide minimal lifting of the surgical instrument (such as a mat or a sheet). An example background surface is found on FIG. 15, which is shown with surgical instruments disposed thereon. Both the load assist device 113 and background surface 128 can be optional.

System 100 may also include one or more optically active articles 108 as described in this disclosure, such as labels, tags, or plates. The optically active article 108 can be attached to or printed on a group of surgical instruments. For example, the group of surgical instruments can be placed in a wrapped package of surgical instruments and the optically active article 108 is placed on the outside of the wrapped package.

In at least one embodiment, the optically active article 108 is disposed proximate to the group of surgical instruments.

The optically active article 108 can be associated with a group of surgical instruments in a datastore 129 (described herein). The wrapped package can be created after the surgical instruments are cleaned and rinsed but prior to sterilization in a sterilizer 125.

In at least one embodiment, the optically active article 108 may have an article message 126 that includes a QR code, bar code, text string or other coded or uncoded visual identifier from the load assist device 113 or background surface 128 to learn information about the bundle. For example, the system may detect a barcode present inside the unwrapped bundle, conclude that all the instruments are expected to be from the same manufacturer or from an expected (small) set of instruments. This information will advantageously reduce the search space for the identification task.

The reflective, non-reflective, and/or retroreflective sheet may be applied to a base surface using one or more techniques and/or materials including but not limited to: mechanical bonding, thermal bonding, chemical bonding, or any other suitable technique for attaching retroreflective sheet to a base surface. A base surface may include any surface of an object (such as described above, e.g., an aluminum plate) to which the reflective, non-reflective, and/or retroreflective sheet may be attached. An article message may be printed, formed, or otherwise embodied on the sheeting using any one or more of an ink, a dye, a thermal transfer ribbon, a colorant, a pigment, and/or an adhesive coated film. In some examples, content is formed from or includes a multi-layer optical film, a material including an optically active pigment or dye, or an optically active pigment or dye.

Article message in FIG. 1 is described for illustration purposes as being formed by different areas that either retroreflect or do not retroreflect light. An article message in FIG. 1 may be printed, formed, or otherwise embodied in an optically active article using any light reflecting technique in which information may be determined from the article message. For instance, article message 126 may be printed using visibly-opaque, infrared-transparent ink and/or visibly-opaque, infrared-opaque ink. Any suitable construction, in which article message 126 or portions thereof are distinguishable under one or more lighting conditions, may be used in accordance with techniques and articles of this disclosure.

In at least one embodiment, the identity type can be a class an instrument 112 (e.g., non-locking forceps). The identity type can also be more specific to the subclass or variety of instrument (e.g., artery forceps). In at least one embodiment, the identity type can be an individual instrument (e.g., instrument number 344444).

In some examples, image capture device 102 is communicatively coupled to computing device 116 via network 114 using one or more communication links. In other examples, as described in this disclosure, image capture device 102 may be communicatively coupled to computing device 116 via one or more forms of direct communication without network 114, such as via a wired or wireless connection that does not require a network.

Figure 16:
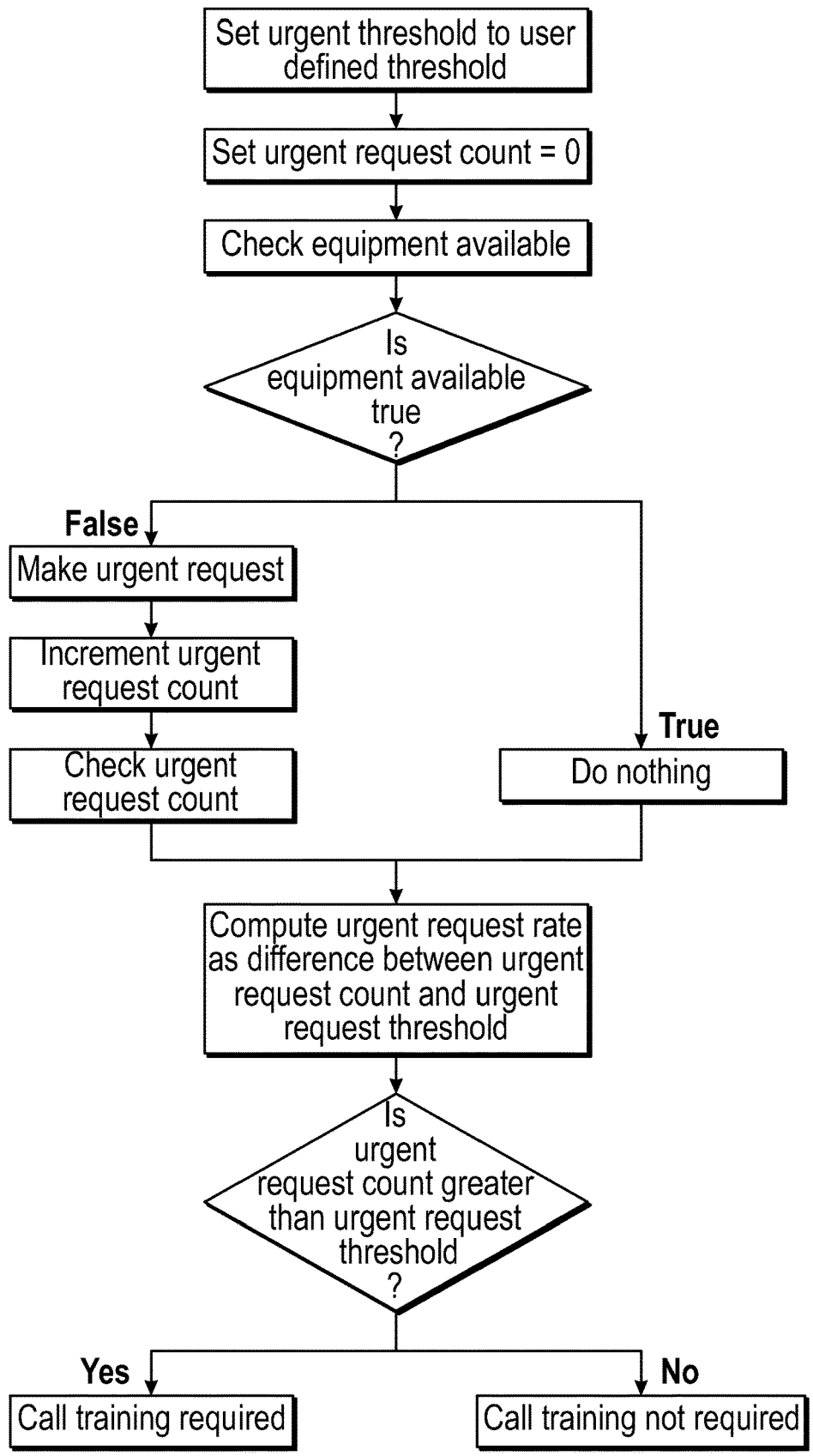
FIG. 16 illustrates a flowchart of a method of determining a training event, according to various embodiments.

Image capture device 102 may convert light or electromagnetic radiation sensed by image capture sensors 106 into information, such as digital image or bitmap comprising a set of pixels. Each pixel may have chrominance and/or luminance components that represent the intensity and/or color of light or electromagnetic radiation. While the image capture device 102 can be any shape and mount in any position, exemplary image capture devices 102 are shown on FIGS. 16 (ceiling mounted), 17 (ceiling mounted, free-standing, or wall mounted), 18 (wall mounted).

In at least one embodiment, a capability of the imaging system to recognize objects (instruments 112) moving "into" or "out of" a given field within the field of vision of the image capture device 102. For example, if a camera is in a fixed mounted position overlooking an OR room, and the sterile field is in a fixed position in the room, could the imaging system demarcate that area within its field of vision and denote an area that's considered "in" that space or "not" in that space (e.g., defined by the area of the background surface 128). The tracking of instruments 112 "into" that field and when it went "out of" that field can imply its use of the instrument (e.g., in an operating room setting).

Image capture device 102 may include one or more image capture sensors 106 and one or more light sources 104. In some examples, image capture device 102 may include image capture sensors 106 and light sources 104 in a single integrated device. In other examples, image capture sensors 106 or light sources 104 may be separate from or otherwise not integrated in image capture device 102. In at least one embodiment, a separate light source 104 can at least be proximate to the image capture device 102. Examples of image capture sensors 106 may include semiconductor charge-coupled devices (CCD) or active pixel sensors in complementary metal-oxide-semiconductor (CMOS) or N-type metal-oxide-semiconductor (NMOS, Live MOS) technologies. Digital sensors include flat panel detectors. In the example, image capture device 102 includes at least two different sensors for detecting light in two different wavelength spectrums. In some embodiments, a first image capture and a second image capture sensor substantially concurrently detect the first and second wavelengths. Substantially concurrently may refer to detecting the first and second wavelengths within 10 milliseconds of one another, within 50 milliseconds of one another, or within 100 milliseconds of one another to name only a few examples. In at least one embodiment, the light source 104 can illuminate the surgical instrument 112 so that uniform lighting is created.

In some examples, one or more light sources 104 include a first source of radiation and a second source of radiation. In some embodiments, the first source of radiation emits radiation in the visible spectrum, and the second source of radiation emits radiation in the near infrared spectrum. In other embodiments, the first source of radiation and the second source of radiation emit radiation in the near infrared spectrum. In at least one embodiment, the first wavelength may be visible light while the second wavelength can be ultraviolet light. In one example, one or more light sources 104 may emit radiation (e.g., light 127) in the near infrared spectrum.

In some examples, image capture device 102 includes a first lens and a second lens. In some examples, image capture device 102 captures frames at 50 frames per second (fps). Other exemplary frame capture rates include 60, 30 and 25 fps. It should be apparent to a skilled artisan that frame capture rates are dependent on application and different rates may be used, such as, for example, 10 or 20 fps. Factors that affect required frame rate are, for example, application (e.g., moving cart vs stationary cart), vertical field of view.

In some examples, image capture device 102 includes at least two channels. The channels may be optical channels. The two optical channels may pass through one lens onto a single sensor. In some examples, image capture device 102 includes at least one sensor, one lens and one band pass filter per channel. The band pass filter permits the transmission of multiple near infrared wavelengths to be received by the single sensor. The at least two channels may be differentiated by one of the following: (a) width of band (e.g., narrowband or wideband, wherein narrowband illumination may be any wavelength from the visible into the near infrared); (b) different wavelengths (e.g., narrowband processing at different wavelengths can be used to enhance features of interest, while suppressing other features (e.g., other objects, sunlight, headlights); (c) wavelength region (e.g., broadband light in the visible spectrum and used with either color or monochrome sensors); (d) sensor type or characteristics; (e) time exposure; and (f) optical components (e.g., lensing).

The image capture device 102 may be stationary or otherwise mounted in a fixed position relative to the surgical instrument 112. For example, the image capture device 102 can be mounted on a workstation, on the ceiling overlooking an individual workstation, etc. In some examples, image capture device 102 may be worn (continuously) or held by a human operator (such as glasses, augmented reality, part of a uniform, or on a lanyard) or robotic device, which changes the position of image capture device 102 relative to the surgical instrument 112.

Image capture device 102 may be communicatively coupled to computing device 116 by one or more communication links 130A and 130B. Image capture device 102 may send images of surgical instrument 112 to computing device 116.

Communication links 130A, 130B, and 130C may represent wired or wireless connections. For instance, communication links 130A and 130B may be wireless Ethernet connections using a WiFi protocol and/or may be wired Ethernet connections using Category 5 or Category 6 cable. Any suitable communication links are possible. In some examples, image capture device 102 is communicatively coupled to computing device 116 by a network 114. Network 114 may represent any number of one or more network connected devices including by not limited to routers, switches, hubs, and interconnecting communication links that provide for forwarding of packet and/or frame-based data. For instance, network 114 may represent the Internet, a service provider network, a customer network, or any other suitable network. In other examples, image capture device 102 is communicatively coupled to computing device 116 by a direct connection, such as Universal Serial Bus (USB) link or other high-speed bus. Although shown separately in FIG. 1, image capture device 102 and computing device 116 may be integrated in a single device or housing. The single device or housing may be attached to a building or other stationary structure, or may not be stationary such that a human operator may carry the single device or housing as a portable structure.

Computing device 116 represents any suitable computing system, which may be remote from or tightly integrated with image capture device 102, such as one or more desktop computers, laptop computers, mainframes, servers, cloud computing systems, etc. capable of sending and receiving information with image capture device 102. In some examples, computing device 116 implements techniques of this disclosure. Using techniques of this disclosure, computing device 116 may determine whether the group of one or more surgical instruments enters or exits the sterilizer 125.

In the example of FIG. 1, computing device 116 includes a technician performance component 117 (which can implement the methods described in FIGS. 13-16), an analysis component 118 (which can perform the image recognition analysis), a data layer 120, service component 122 and user interface (UI) component 124. An analysis component 118 can receive an image, convert the image into one or more feature values, and determine the instrument type of the surgical instrument in the image. The analysis component 118 can further query a datastore 129 to receive information related to the surgical instrument.

Further, the computing device 116 can be communicatively coupled to a datastore 129 via the network 114 or a direct connection. The datastore 129 may store data in structure or unstructured form. Example datastores may be any one or more of a relational database management system, online analytical processing database, table, or any other suitable structure for storing data.

The datastore 129 can have one or more records 132 which are associated with a group of one or more surgical instruments 112. The record 128 for surgical instruments 112 can be accessed based on the input from the image capture device 102. For example, after every entry or exit of the group of one or more surgical instruments 112 into or out of the sterilizer (which is detected by the image capture device 102 identifying the surgical instrument 112), the record 132 for any individual surgical can be subject to a record management operation. In at least one embodiment, comparing a surgical instrument 112 to a record 132 in the database for comparison purposes will help determine the number of uses for that particular instrument (through how many times this instrument has been seen by vision system 100) and can allow for better maintenance planning and inventory management.

The record management operation is any operation that changes the record (e.g., creates a new attribute or record, modifies an attribute of an existing record, or deletes an attribute). In at least one embodiment, the record management operation includes modifying a record in the datastore for the one or more surgical instruments that the one or more surgical instruments are present (e.g., in a package). In the example above, a record for each surgical instrument in the group can be updated to indicate that the surgical instrument was sterilized (or at least placed in the sterilizer) upon both check-in and check-out of the group from the sterilizer.

While information related to static data is constant and non-updatable, information related to a surgical instrument may be updated. In one instance, where database is integrated with or part of a machine vision system, information related to surgical instrument (s) may be updated on a regular and recurring basis, such as downloaded through network 114 daily. In one instance, information related to a surgical instrument may be stored in a centralized datastore 129 connected to a network that allows multiple individuals or entities to update information related to surgical instrument. Machine vision systems or other entities requiring access to information related to surgical instruments can then update information from the centralized datastore 129 so that it can be stored locally and a local copy can be accessed in real time, independent of an accessible network connection. In another instance, a machine vision system may connect with and communicate through network 114 to query a database or a centralized datastore 129 storing information related to surgical instrument (s). In some examples, a computing device may query multiple different databases, and in some examples, the datastore 129 queried from the multiple different datastores may be based at least in part on data included for the surgical instrument.

Information related to surgical instruments can include a wide range of information. Some examples of information related to surgical instruments are: a condition of the article, a condition of the physical area near the article, identifying information for a person to whom the article is assigned, instructions for a user of the article, and instructions for an individual or device in proximity to the article.

Service component 122 may provide any number of services, by performing one or more operations. For instance, service component 122, upon receiving an instrument type may generate one or more alerts, reports, or other communications that are sent to one or more other computing devices. Such alerts may include but are not limited to: emails, text messages, lists, phone calls, or any other suitable communications.

In some examples, user interface (UI) component 124 may act as an intermediary between various components and optical elements of computing device 116 to process and send input detected by input devices to other components and optical elements, and generate output from other components and optical elements that may be presented at one or more output devices. For instance, UI component 124 may generate one or more user interfaces for display, which may include data and/or graphical representations of alerts, reports, or other communications.

Components 118, 120, 122, and 124 may perform operations described herein using software, hardware, firmware, or a mixture of both hardware, software, and firmware residing in and executing on computing device 116 and/or at one or more other remote computing devices. In some examples, components 118, 120, 122, and 124 may be implemented as hardware, software, and/or a combination of hardware and software. Computing device 116 may execute components 118, 120, 122, and 124 with one or more processors.

Computing device 116 may execute any of components 118, 120, 122, and 124 as or within a virtual machine executing on underlying hardware. Components 118, 120, 122, and 124 may be implemented in various ways. For example, any of components 118, 120, 122, and 124 may be implemented as a downloadable or pre-installed application or "app." In another example, any of components 118, 120, 122, 124 may be implemented as part of an operating system of computing device 116. In any case, components 118, 120, 122, and 124 may execute at or be implemented at computing devices described herein, which may be an example of computing device 116.

In at least one embodiment, the datastore 129 can include a content datastore (not shown) that may include a series of bits consisting of the payload from content optical elements and the information associated with those series of bits. In some examples, the content datastore may include messages in encoded or decoded form. The datastore 129 can also include a context datastore (not shown) which may include a series of bits consisting of the payload from context optical elements and the information associated with those series of bits. In some examples, the context datastore may include messages in encoded or decoded form. The datastore 129 can also include Error Correction Data which may include series bits forming codewords constructed by the error correction algorithm which aids in reconstruction and verification of payload data found in the content optical elements and context optical elements. The datastore 129 can include service data which may include any data to provide and/or resulting from providing a service of service component. For instance, service data may include information about optically active articles (e.g., sterilization check-in/out), user information, or any other information.

In at least one embodiment, an image of the surgical instrument 112 is captured with light in the visible light spectrum. In some examples, a first spectral range is from about 350 nm to about 700 nm (i.e., visible light spectrum) and a second spectral range is from about 700 nm to about 1 100 nm (i.e., near infrared spectrum). In some examples, a first spectral range is from about 700 nm to about 850 nm, and a second spectral range is between 860 nm to 100 nm. In another example, the first or second spectral range can be ultraviolet spectrum (10 nm to 400 nm) which can also further sterilize the one or more surgical instruments. When an image is generated, the visible light 127 is retroreflected back to image capture device 102. As a result of receiving the retroreflected light, article message 126 may appear black, while portions other than article message 126 may appear white or bright relative to. In at least one embodiment, the image capture device 102 can capture only visible light.

In some examples, the first lighting condition includes a first range of wavelengths and the second lighting condition includes a second range of wavelengths that is substantially different from the first range of wavelengths. In some examples, first and second ranges of wavelengths may be substantially different if less than 1% of the wavelengths are the same in each range of wavelengths. In some examples, first and second ranges of wavelengths may be substantially different if the fewer than between 1% and 10% of the wavelengths are the same in each range of wavelengths. In some examples, first and second ranges of wavelengths may be substantially different if the number of wavelengths are the same in each range is less than a threshold amount.

In some examples, a second image may be captured under UV lighting. For an image of surgical instrument 112 captured under UV lighting conditions, soil or other contaminants may be more visible to the image capture device 102.

The system 100 can also include various analytical devices 140 that communicate with the computing device 116 secondary properties of the surgical instrument 112. The properties of the surgical instrument 112 can be associated with a record 132 for the surgical instrument.

The analytical devices 140 can include an indicator 134 and a scale 136. In at least one embodiment, the computing device 116 can receive a status of the indicator 134 from the image capture device 102. For example, the indicator 134 can be a chemical indicator 134 that is embedded, attached to, or proximate to the optically active article 108. An example of an indicator 134 is commercially available under the trade designation Comply from 3M (St Paul, Minn.). The computing device 116 can determine whether the chemical indicator is present with the one or more surgical instruments based on first image or the second image and determine the status of the chemical indicator 134 from the first or second image. In at least one embodiment, the computing device 116 can perform at least one operation in response to the determination of the presence or status of the chemical indicator 134 (e.g., modify a record for the one or more surgical instruments in the group). In at least one embodiment, the indicator portion of the is responsive to an environmental condition.

In at least one embodiment, the indicator 134 would be detected by the computing device 116 at two-time points in a workflow associated with reprocessing and use of the instruments in a given load assist device 113: 1) at the time the load assist device 113 is assembled after decontamination of the instruments 112 and prior to being wrapped with a nonwoven sheet, and 2) at the time that a nonwoven sheet containing the surgical instrument 112 is opened in the operating room and the contents of the tray are available for use.

In the first instance above, the vision system 100 can verify that a technician assembling the load assist device 113 had in fact placed the chemical indicator 134 in the load assist device 113 prior to wrapping it. This would ensure that a wrapped load assist device 113 would not be later opened in an operating room only to find out that there was a missing chemical indicator 134 in that load assist device 113 which would require reprocessing of the surgical instrument 112. This can create havoc and a significant delay in the OR, especially if the tray contains specialized instrumentation.

In the second instance above, the vision system 100 would be used to detect and log the actual result (pass/fail) from that chemical indicator 134 automatically providing updates to the record 132 for the instrument 112. The chemical indicator 134 can use a similar detection method as the instrument 112. The chemical indicator 134 shape can be treated as another shape to detect. A machine learning classifier, for example a multiclass logistic regression classifier, would be trained to distinguish multiple surgical instruments 112 from each other, and be able to distinguish the appearance of the chemical indicator 134 from that of the surgical instrument 112.

In at least one embodiment, the machine vision system 100 can also include a computing device 138. The computing device 138 can also be a client device to the computing device 116. Although one computing device 138 is shown, multiple computing devices 138 can exist in the system. The computing device 138 can be a laptop, smart phone, augmented reality device, virtual reality device, or other device that receives information and processes the information in a machine-readable format. The computing device 138 can receive templates from the datastore 129 and display the video feed from the image capture device 102. In at least one embodiment, the computing device 138 can also have a bar code scanner. The computing device 138 can receive alerts communicated from the computing device 116. For example, if a surgical instrument is missing from an operating room, then the computing device 116 can alert computing device 138 which is carried by a technician. The technician can promptly retrieve the surgical instrument from one part of the hospital and deliver the instrument to the operating room.

Figure 2:
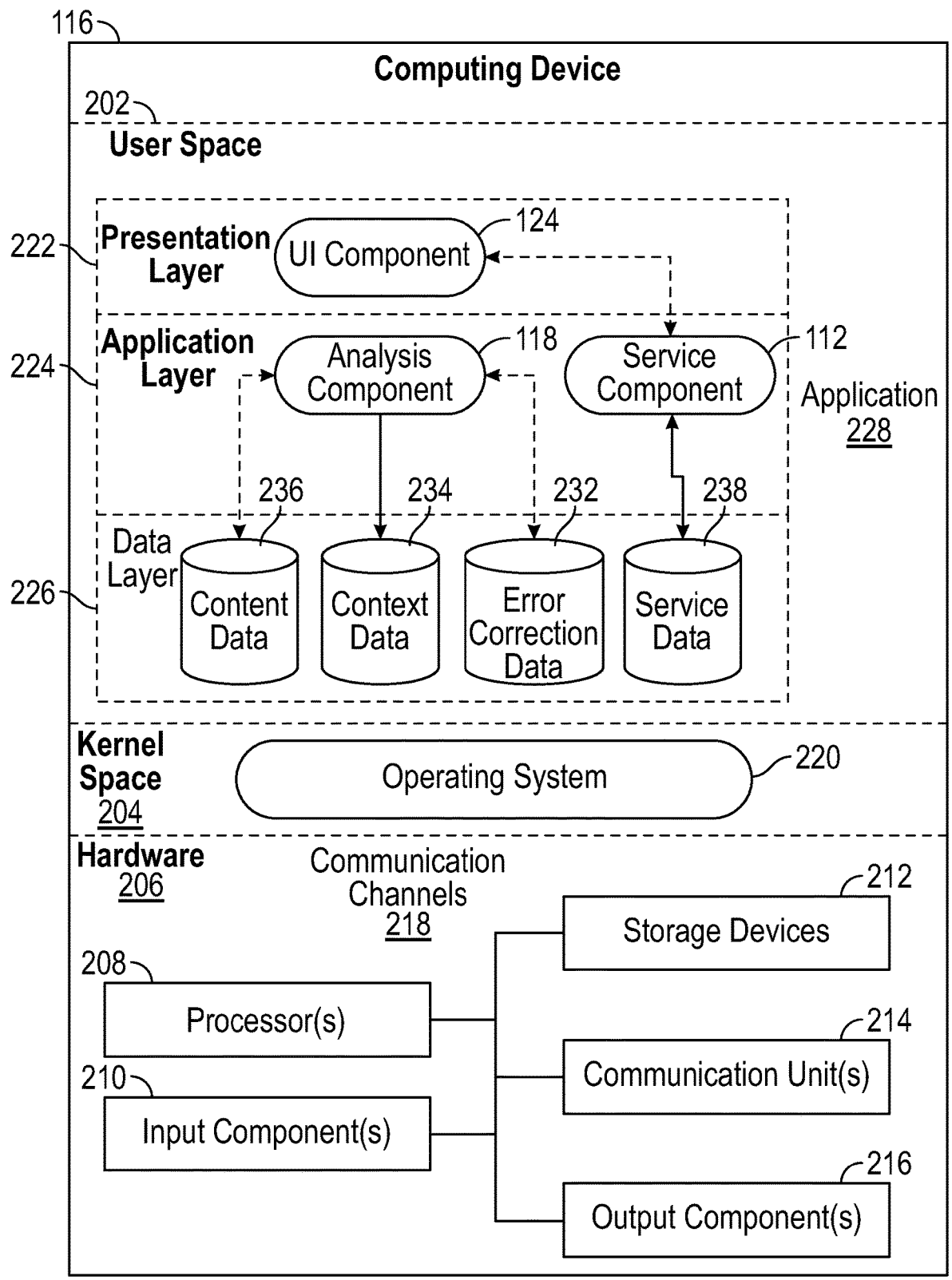
FIG. 2 illustrates a block diagram of a computing device useful in performing aspects of the present disclosure.

FIG. 2 is an example of a computing device for use in a dynamic system for determining an instrument type. FIG. 2 illustrates only one particular example of computing device 116, as shown in FIG. 1. Many other examples of computing device 116 may be used in other instances and may include a subset of the components included in example computing device 116 or may include additional components not shown example computing device 116 in FIG. 2. In some examples, computing device 116 may be a server, tablet computing device, smartphone, wrist- or head-worn computing device, laptop, desktop computing device, or any other computing device that may run a set, subset, or superset of functionality included in application 228.

As shown in the example of FIG. 2, computing device 116 may be logically divided into user space 202, kernel space 204, and hardware 206. Hardware 206 may include one or more hardware components that provide an operating environment for components executing in user space 202 and kernel space 204. User space 202 and kernel space 204 may represent different sections or segmentations of memory, where kernel space 204 provides higher privileges to processes and threads than user space 202. For instance, kernel space 204 may include operating system 220, which operates with higher privileges than components executing in user space 202.

As shown in FIG. 2, hardware 206 includes one or more processors 208, input components 210, storage devices 212, communication units 214, and output components 216. Processors 208, input components 210, storage devices 212, communication units 214, and output components 216 may each be interconnected by one or more communication channels 218. Communication channels 218 may interconnect each of the components 208, 210, 212, 214, and 216 for inter-component communication (physically, communicatively, and/or operatively). In some examples, communication channels 218 may include a hardware bus, a network connection, one or more inter-process communication data structures, or any other components for communicating data between hardware and/or software.

One or more processors 208 may implement functionality and/or execute instructions within computing device 116. For example, processors 208 on computing device 116 may receive and execute instructions stored by storage devices 212 that provide the functionality of components included in kernel space 204 and user space 202. These instructions executed by processors 208 may cause computing device 216 to store and/or modify information, within storage devices 212 during program execution. Processors 208 may execute instructions of components in kernel space 204 and user space 202 to perform one or more operations in accordance with techniques of this disclosure. That is, components included in user space 202 and kernel space 204 may be operable by processors 208 to perform various functions described herein.

One or more input components 210 of computing device 116 may receive input. Examples of input are tactile, audio, kinetic, and optical input, to name only a few examples. Input components 242 of computing device 216, in one example, include a mouse, keyboard, voice responsive system, video camera, buttons, control pad, microphone or any other type of device for detecting input from a human or machine. In some examples, input component 210 may be a presence-sensitive input component, which may include a presence-sensitive screen, touch-sensitive screen, etc.

One or more output components 216 of computing device 116 may generate output. Examples of output are tactile, audio, and video output. Output components 216 of computing device 116, in some examples, include a presence-sensitive screen, sound card, video graphics adapter card, speaker, cathode ray tube (CRT) monitor, liquid crystal display (LCD), or any other type of device for generating output to a human or machine. Output components may include display components such as cathode ray tube (CRT) monitor, liquid crystal display (LCD), Light-Emitting Diode (LED) or any other type of device for generating tactile, audio, and/or visual output. Output components 216 may be integrated with computing device 116 in some examples. In other examples, output components 216 may be physically external to and separate from computing device 116, but may be operably coupled to computing device 116 via wired or wireless communication. An output component may be a built-in component of computing device 116 located within and physically connected to the external packaging of computing device 116 (e.g., a screen on a mobile phone). In another example, presence-sensitive display 202 may be an external component of computing device 116 located outside and physically separated from the packaging of computing device 116 (e.g., a monitor, a projector, etc. that shares a wired and/or wireless data path with a tablet computer).

One or more communication units 214 of computing device 116 may communicate with external devices by transmitting and/or receiving data. For example, computing device 116 may use communication units 214 to transmit and/or receive radio signals on a radio network such as a cellular radio network. In some examples, communication units 214 may transmit and/or receive satellite signals on a satellite network such as a Global Positioning System (GPS) network. Examples of communication units 214 include a network interface card (e.g. such as an Ethernet card), an optical transceiver, a radio frequency transceiver, a GPS receiver, or any other type of device that can send and/or receive information. Other examples of communication units 214 may include Bluetooth®, GPS, 3G, 4G, and Wi-Fi® radios found in mobile devices as well as Universal Serial Bus (USB) controllers and the like.

One or more storage devices 212 within computing device 116 may store information for processing during operation of computing device 116. In some examples, storage device 212 is a temporary memory, meaning that a primary purpose of storage device 212 is not long-term storage. Storage devices 212 on computing device 116 may configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art.

Storage devices 212, in some examples, also include one or more computer-readable storage media. Storage devices 212 may be configured to store larger amounts of information than volatile memory. Storage devices 212 may further be configured for long-term storage of information as non-volatile memory space and retain information after activate/off cycles. Examples of non-volatile memories include magnetic hard discs, optical discs, floppy discs, flash memories, or forms of electrically programmable memories (EPROM) or electrically erasable and programmable (EEPROM) memories. Storage devices 212 may store program instructions and/or data associated with components included in user space 202 and/or kernel space 204.

As shown in FIG. 2, application 228 executes in user space 202 of computing device 116. Application 228 may be logically divided into presentation layer 222, application layer 224, and data layer 226. Presentation layer 222 may include user interface (UI) component 124, which generates and renders user interfaces of application 228. Application 228 may include, but is not limited to: UI component 124, algorithm coding component 542, data layer 226, and one or more service components 546. Presentation layer 222 may include UI component 124.

Data layer 226 may include one or more datastores (defined herein). Content datastore 234 may include: a series of bits consisting of the payload from content optical elements and the information associated with those series of bits. In some examples, content datastore 234 may include messages in encoded or decoded form. Context datastore 236 may include a series of bits consisting of the payload from context optical elements and the information associated with those series of bits. In some examples, context datastore 234 may include messages in encoded or decoded form. Error Correction Data 232 may include series bits forming codewords constructed by the error correction algorithm which aids in reconstruction and verification of payload data found in the content optical elements and context optical elements. Service data 238 may include any data to provide and/or resulting from providing a service of service component 122. For instance, service data may include information about optically active articles (e.g., vehicle registration information), user information, or any other information.

A machine vision system 100 may capture an image including the surgical instrument, determine an instrument type and communicate it to computing device 116 through UI component 124 or communication channels. Service component 122 may perform one or more operations based on the data generated by analysis component 118, such as send data to UI component 124 that causes UI component 124 to generate an alert for display. Other operations may include generating a report or storing a message based on data generated by an analysis component 118. In some examples, service component 122 may modify the record 132 of a central datastore 129

While one particular implementation of a computing system is described herein, other configurations and embodiments of computing systems consistent with and within the scope of the present disclosure will be apparent to one of skill in the art upon reading the present disclosure.

Figure 3:
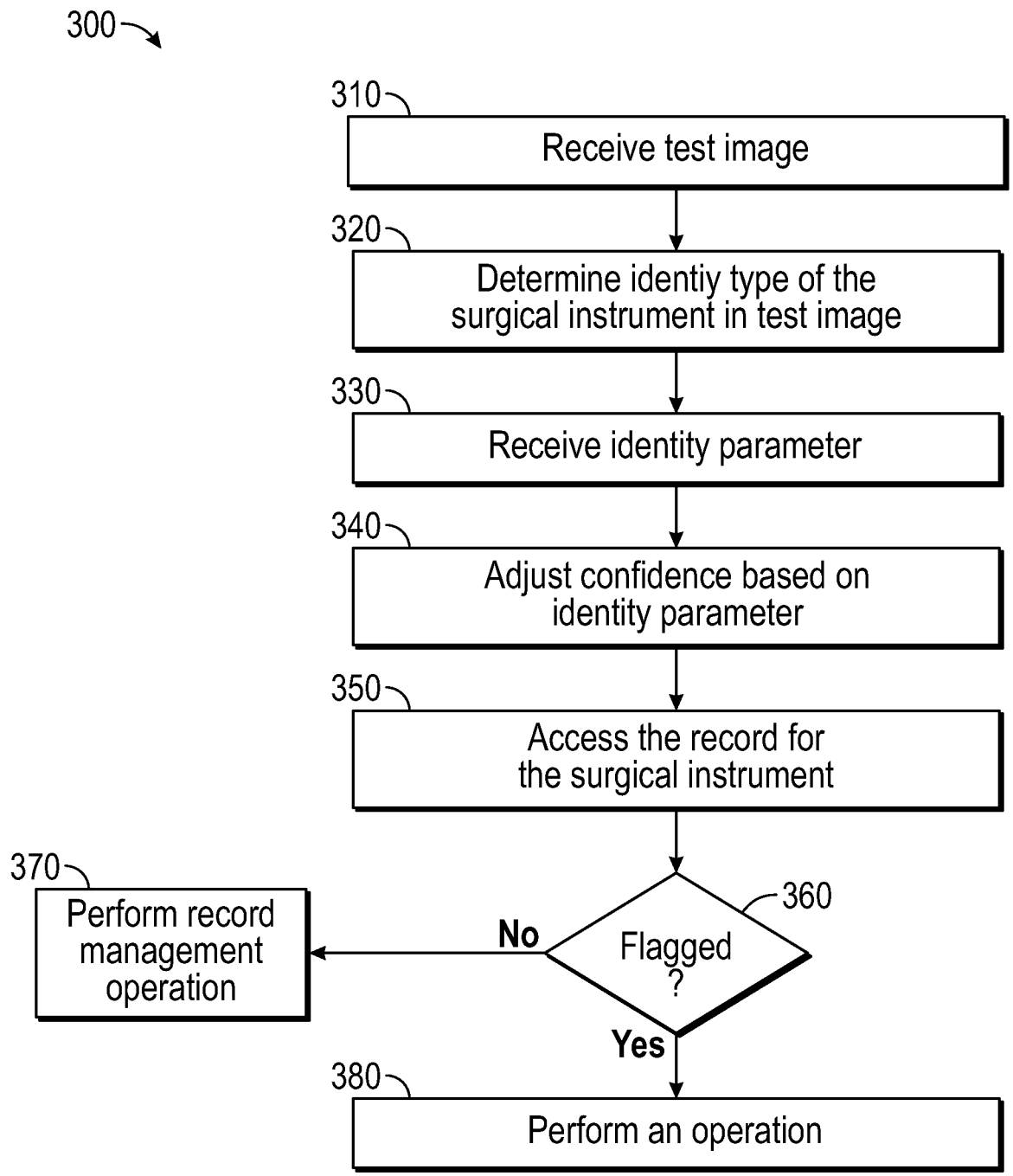
FIG. 3 illustrates a flowchart of a method of performing an operation in response to a flagged event, according to various embodiments.

FIG. 3 is a flowchart of a method 300 of conducting an inventory. At least a portion of the method can be implemented by the computing device described herein.

In block 310, the computing device can receive a test image from the image capture device or from the datastore or a remote source. The test image can correspond to a surgical instrument. The test image can include one or more images of the surgical instrument and received as a video feed from the image capture device. In at least one embodiment, the test image can be retrieved from the datastore and be relevant where a technician encounters an unknown instrument having an unlabeled image and wants to determine the identity at a later time. This can be particularly useful during training.

In block 320, the computing device can determine an identity type of the surgical instrument using the test image in a machine vision technique. Machine vision techniques can be described in the copending provisional application titled "Machine vision system for surgical instrument identification", which is incorporated by reference in its entirety. The machine vision techniques described herein can also be used to identify a chemical indicator and a status of the chemical indicator.

Figure 5:
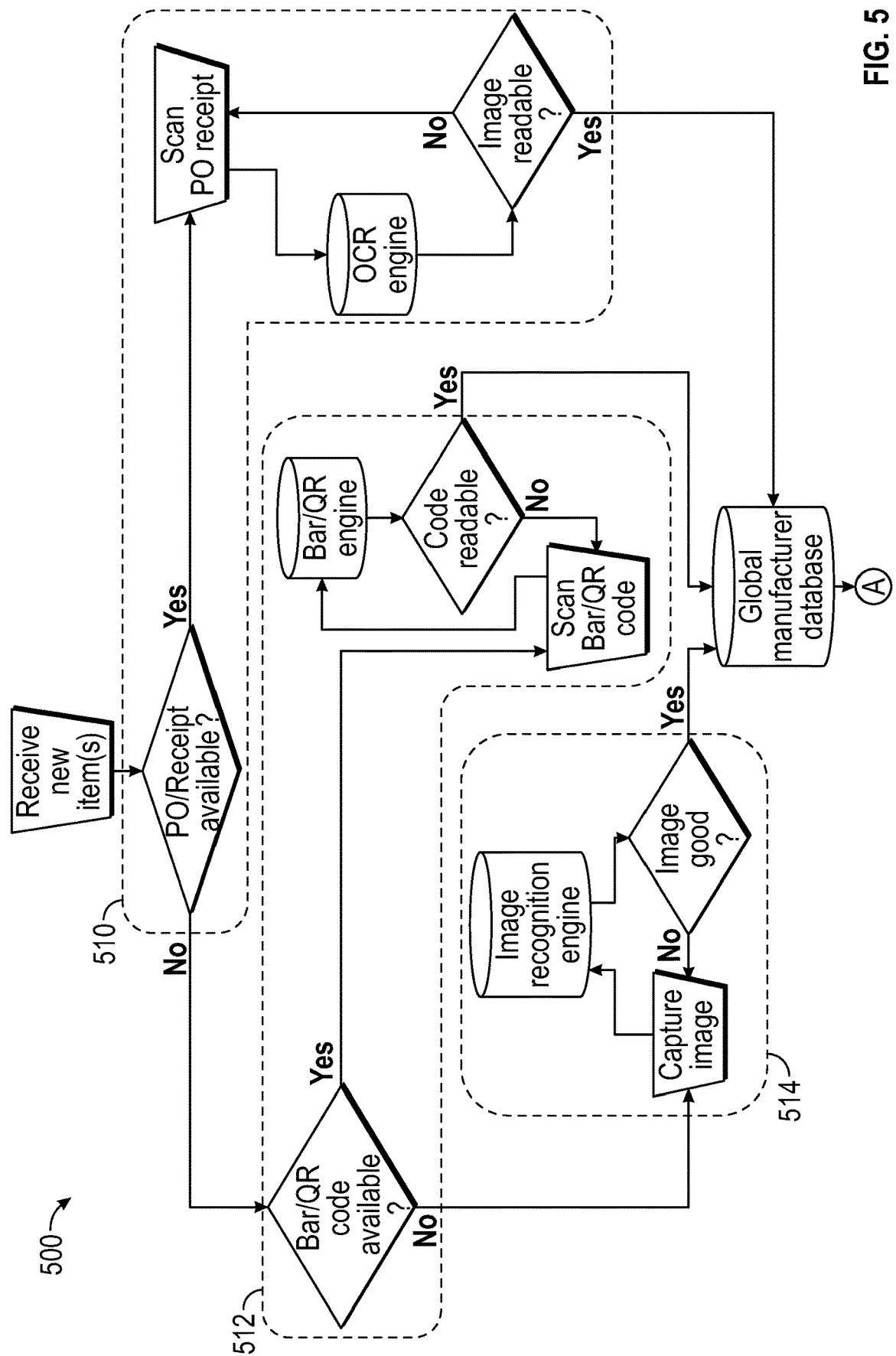
FIG. 5 illustrates a flowchart of a method of managing identification of a surgical instrument, according to various embodiments.
Figure 6:
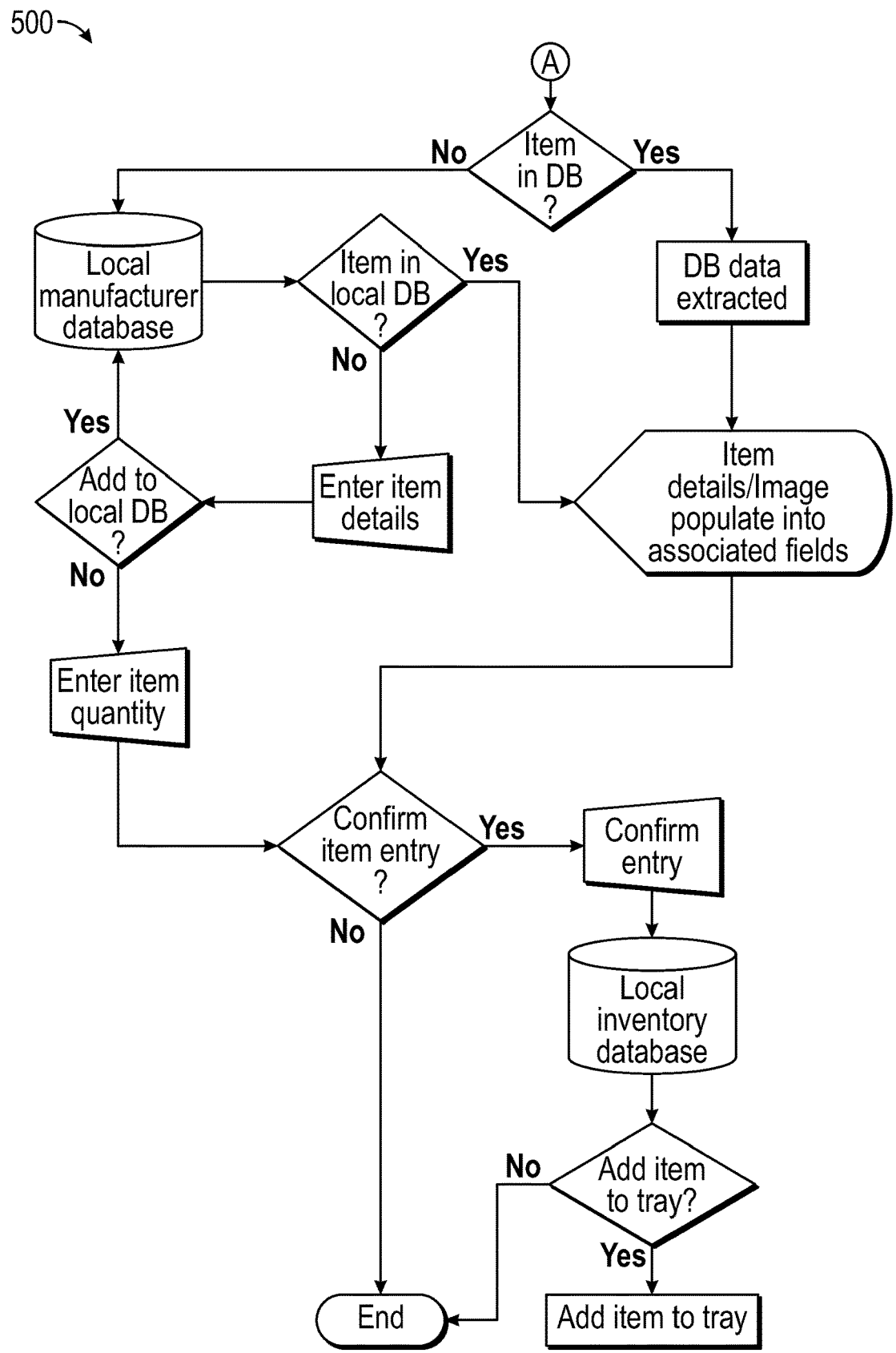
FIG. 6 illustrates a continuation of the method of FIG. 5, according to various embodiments.

An embodiment of an overall inventory management method is found on FIGS. 5 and 6. In at least one embodiment, the determining of the identity type can be conditional based on the surgical instrument not being previously labeled. This can save computing resources for unlabeled or untagged surgical instruments by reducing function calls to the machine vision system.

For example, turning to FIG. 5, new items can be received for intake into the inventory database. If a PO or package receipt is available, that artifact can be scanned using a device that runs the image against an OCR engine that interprets the image to parse out the information into individual text content that is then matched against a Global Manufacturer database (GMDB) to find a match. If there is a match, the details for each line item is automatically generated and populated into the system. If the image cannot be interpreted, the user can either recapture an image to repeat the process, or the user can manually identify the item(s) against the GMDB. If no PO or package receipt is available, the user may be able to use each item's bar code or assigned QR code to match against the GMDB. If there are no bar codes or QR codes, the user may capture an image of the item(s) itself/themselves, which is then sent to an Image Recognition Engine (IRE) that analyses the image to match against the GMDB. If the IRE cannot establish a match, or the user cannot capture an image, the user can ultimately manually find the item in the GMDB or create a new item entry into the facility's Local Manufacturer database (LMDB). Once all items have been properly identified by the system, those items are now ready to be associated to corresponding trays as needed.

Figure 19:
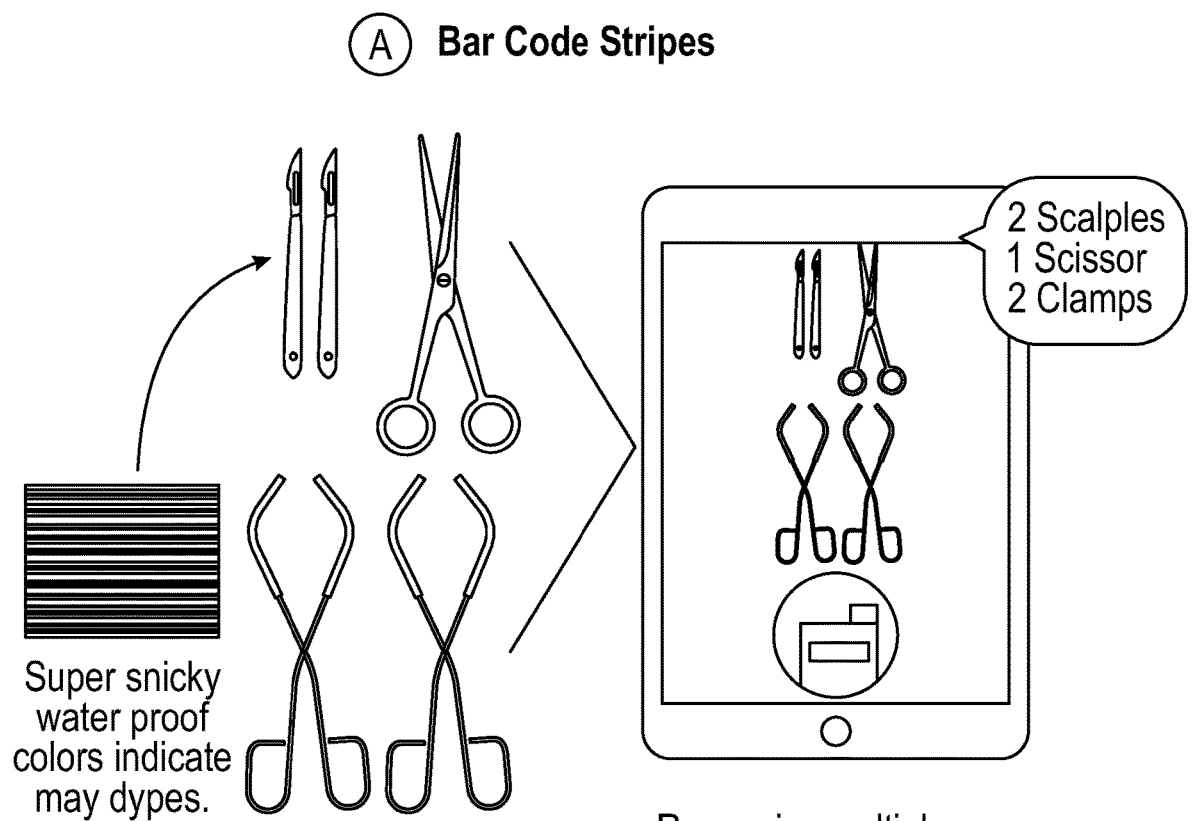
FIG. 19 illustrates an image of an article message using bar code strips, according to various embodiments.

In at least one embodiment, the computing device can determine, with the image capture device, whether an article message is present on a surgical instrument as described in process group 512, and determine the identity type of the first surgical instrument using a machine vision technique based on whether the article message is present as shown in process group 514. As discussed herein, the article message can be a bar code, QR code, visual indication of an alphanumeric sequence, or combinations thereof. An exemplary bar code can further comprise a color-coded bar code stripes as shown in FIG. 19.

Returning to FIG. 5, the computing device can also determine whether the article message is present occurs responsive to determining if a receipt or purchase order is available for the device as shown in process group 510. If available, the computing device adding the receipt or purchase order to the record for the surgical instrument. In at least one embodiment, the purchase order can be used to identify the surgical instrument via optical character recognition.

Returning to FIG. 3, in block 330 and 340, the computing device can receive and identity parameter which can be used to add confidence to the identity of the instrument type. The identity parameter can be a secondary identity which helps aid the identification of the test image. For example, a scale can be used to determine mass of the surgical instrument which can be paired with the image analysis to increase confidence in the overall model.

Once determined, the computing device can adjust a confidence of the determination of the identity type based on an identity parameter. For example, item mass and refraction index can be paired with the machine vision analysis of the image to increase confidence in the assessment.

In block 350, the computing device can access a record for a surgical instrument. The record can be maintained in a datastore as discussed herein.

In block 360, the computing device can determine whether the first surgical instrument is flagged. In at least one embodiment, a flag is a condition associated with the record for the surgical instrument that indicates to the computing device to perform an operation. The condition can be conditional operation derived from the one or more records from the datastore. In at least one embodiment, the flag is generated by the computing component based on attributes within the datastore. While many types of flags can exist, for the purposes of illustration, only a few flags will be discussed.

For example, a flag can be based on special handling instructions for the surgical instrument. A difficult to clean surgical instrument can be flagged based on cleanliness results from a biological, chemical indicator, or an ATP-based indicator. The record can be flagged by the system automatically as a result of receiving special cleaning instructions from a manufacturer. An operation that can be triggered upon receiving the flag is to present the special handling instructions on the display.

A flag can also be based on an urgent request. For example, a surgical instrument may be checked-in but another surgical instrument of the same type is urgently needed in an operating room. Thus, the operation can be to display a notification of the urgency and a location of where the surgical instrument is needed. Thus, the flag can also be based on whether an instrument is missing from a group of surgical instruments in a different location. The computing device can also be configured to present the group and a location associated with the group. The flag can also identify that the encountered surgical instrument is a lost instrument and display ownership of the instrument (i.e., return to manufacturer).

A flag can also be based on a record for the first surgical instrument not being present in the datastore. The record the surgical instrument in the datastore is updated from a plurality of secondary sources as shown in FIG. 18.

Figure 18:
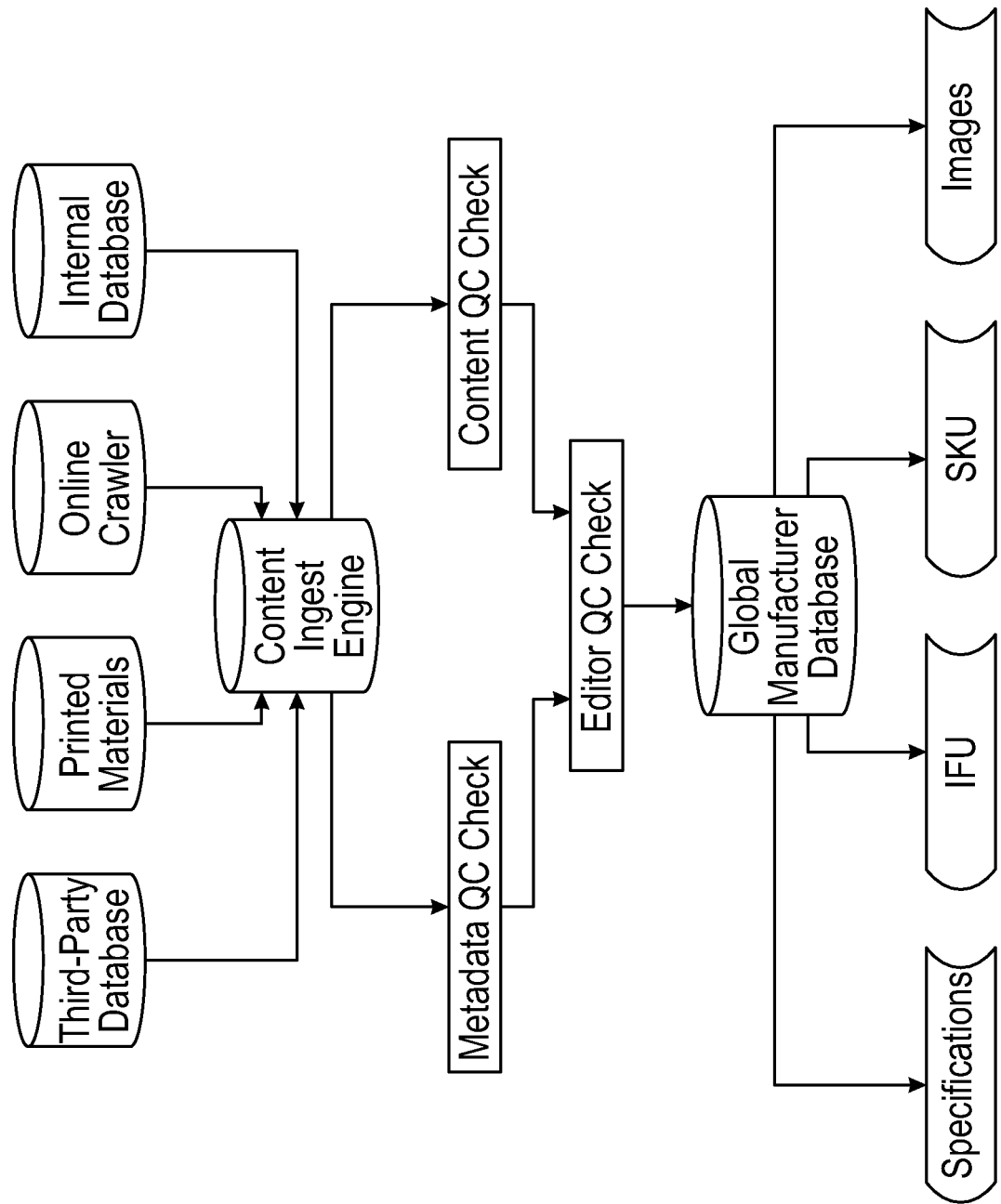
FIG. 18 illustrates a block diagram of a datastore management process, according to various embodiments.

For example, FIG. 18 shows a global manufacturing database (GMDB) which is a system that aims to incorporate a comprehensive database of manufacturer details for all known relevant instrument, devices, and equipment. This allows users with access to the system to be able to access any detail concerning an instrument or piece of equipment from technical specifications to detailed instructions for use. This comprehensive collection of data on all relevant manufacturer products is enabled through two key processes: an ingest pathway known as the Content Ingest Engine (CIE), which incorporates multiple content ingest channels, both manual and automated; and an extensive editorial system which uses both automated and human-editor quality checks, to validate, categorize, and curate the ingested content.

Content that is processed by the CIE is collected through a variety of pathways. One such way is through the access of online digital databases including internal databases, and external third-party databases. Content from those databases are captured using an online crawler that will crawl them at regular intervals to capture new content and validate existing content for accuracy and timeliness. Another method is through physical, printed materials. This is done using a scanning process that incorporates a variety of other technology engines to interpret and analyze those printed artifacts to parse out any relevant information for processing by the CIE.

Once ingested, the CIE analyzes and parses out all relevant data points to categorize them into their appropriate domains based on identified schemas and taxonomies known to the CIE. That content is then reviewed and edited by human Quality Control Editors (QCE) to ensure all data sets are properly identified and categorized. A final check is done by principle editors to validate all work done by both the CIE and the QCEs before becoming staged for release to the GMDB. Finally, once all data is properly vetted and staged, it is released to the GMDB and made accessible by any users of the system.

If the encountered surgical instrument is not present in the datastore (i.e., the first encounter for the surgical instrument), then the computing device can perform a record management operation to the record for the first surgical instrument based on the determination of the identity type. The record management operation can include adding the record to the datastore, adding details associated with the first surgical instrument manually, or combinations thereof.

A flag can be based on an economic status of the surgical instrument. For example, the economic status can refer to the cost of the instrument, rarity, or the contractual status (i.e., under loan, purchased, or free).

The flag can be based on whether the surgical instrument is part of a wrapped package. For example, if the surgical instrument is identified as being associated with the wrapped package, the computing device can determine whether a chemical indicator is present with the surgical instrument using a machine vision technique as a subsequent operation. The record for the wrapped package is updated to indicate the presence of the chemical indicator.

The flag can also be based on the technician performing the check-in, check-out, assembly, opening, or combinations thereof. For example, a technician record/profile may have been flagged for previous retraining as provided in FIG. 13. Thus, multiple actions from the flagged technician can be met with strict scrutiny such as repeated verification prompts through critical process steps or even every step. In at least one embodiment, the flag can cause the computing device track performance data of a technician as shown in FIG. 14.

Figure 14:
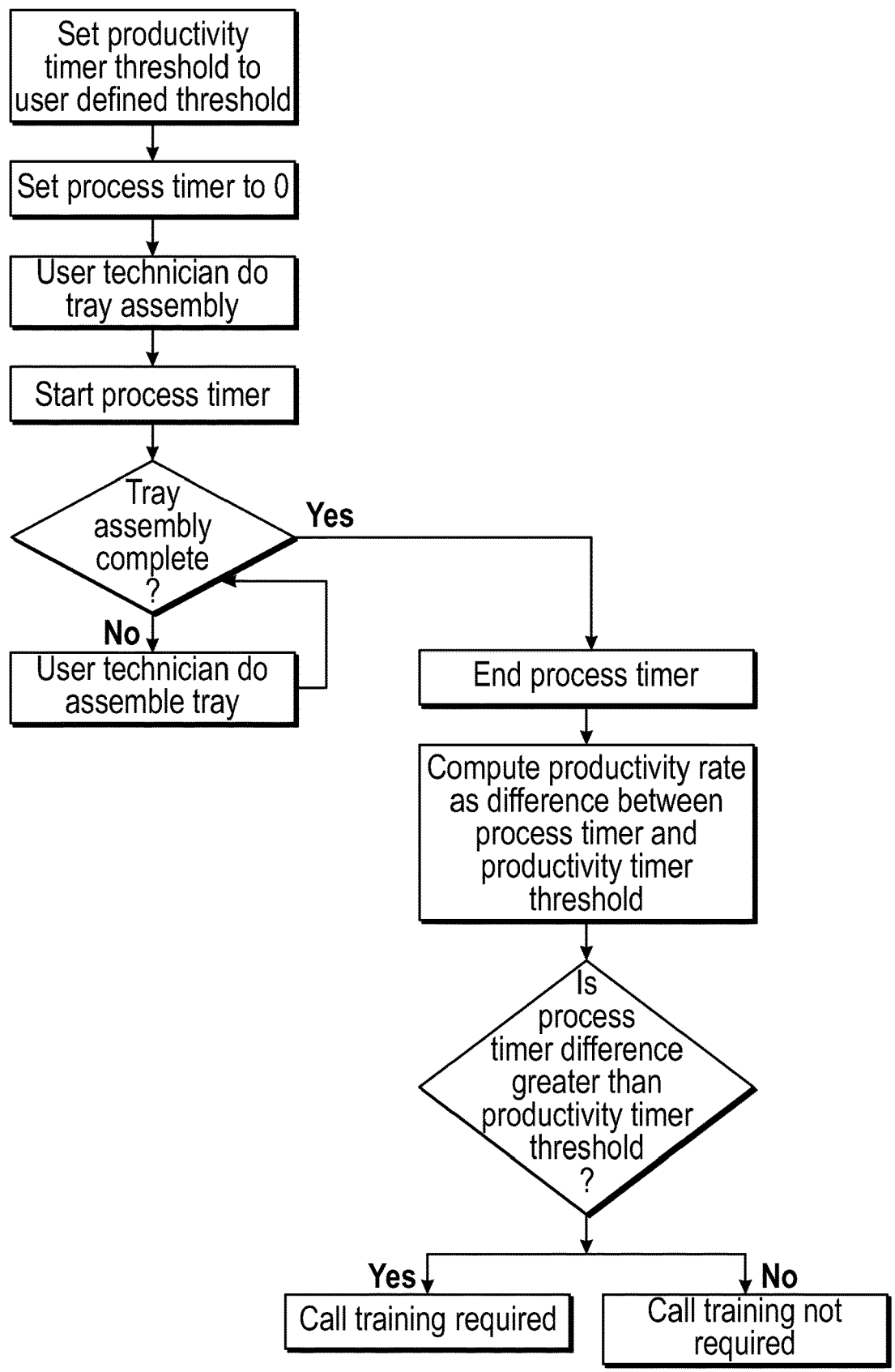
FIG. 14 illustrates a flowchart of a method of determining a training event, according to various embodiments.

For example, in FIG. 14, interactions made by users (such as technicians) can be monitored, tracked, and analyzed using a series of metrics to ascertain performance levels based on defined thresholds. If those thresholds are not met by particular users, they will be provided with new or remedial training curriculum developed for them through their analyzed data, personalizing that training to that specific individual. Examples of such metrics include checks against a user's productivity, their repeated need to access instrument information, urgent requests made by an operating room for specified instruments that were not available at the time of procedure, or number of flash sterilizations required for an improperly cleaned instrument.

Figure 13:
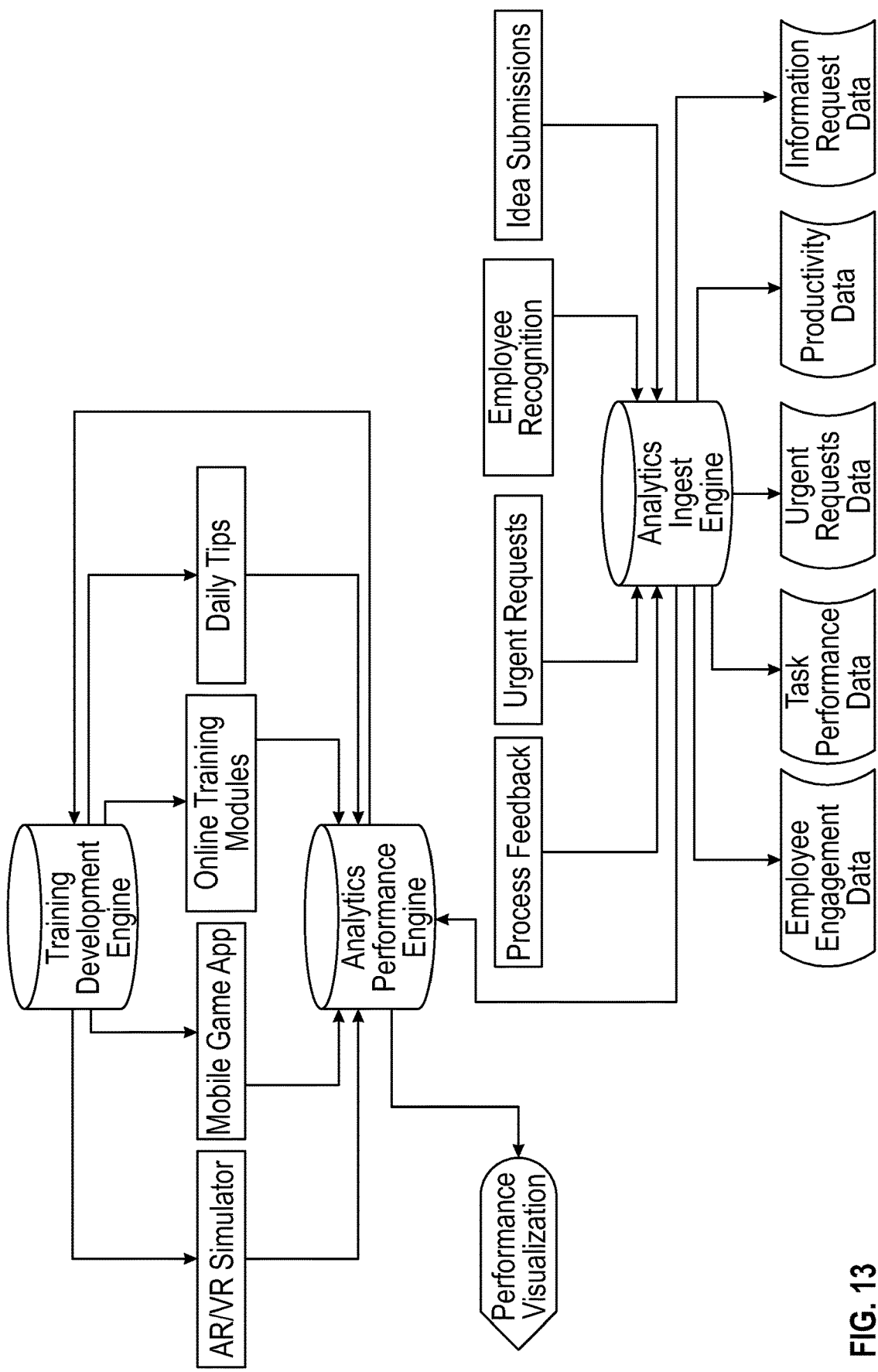
FIG. 13 illustrates a block diagram of a training process, according to various embodiments.

The record associated with the technician can be updated continuously from a variety of sources (FIG. 13). For example, in FIG. 13, interactions within this system are being tracked to analyze performance and accuracy based on a variety of key metrics. Those metrics are assessed through a variety of other subsystems and are feed in to an Analytics Ingest Engine (AIE). The AIE captures data from those subsystems and quantifies them into a format that can be analyzed by an Analytics Performance Engine (APE). The APE analyzes the data ingested by the AIE to assess a variety of performance metrics at both the individual level and wider facility and system level. Trends identified by the APE are then forwarded to the Training Development Engine (TDE) to develop training curriculum necessary for individuals who need additional or remedial training. The APE also sends that data to any user-identified dashboards so that managers and directors can review those data sets and trends for reporting and analytics purposes.

Training curriculum developed by the TDE are assigned to those users in need through a multi-channel system that incorporates a variety of modes and mediums, such as immersive AR or VR environments, desktop online training, or more personalized daily activities through a user's personal mobile device.

Each mode will have specific modules that maximizes the learning opportunity of those modes and weighs each mode accordingly to ensure that learning is maximized through each mode individually, but also that lack of access to a particular mode does not inhibit a user's ability to complete the curriculum developed.

Completion of the curriculum is analyzed by the APE to reassess the user in question and those data points are then returned to the TDE to further evaluate any need for additional training.

Figure 15:
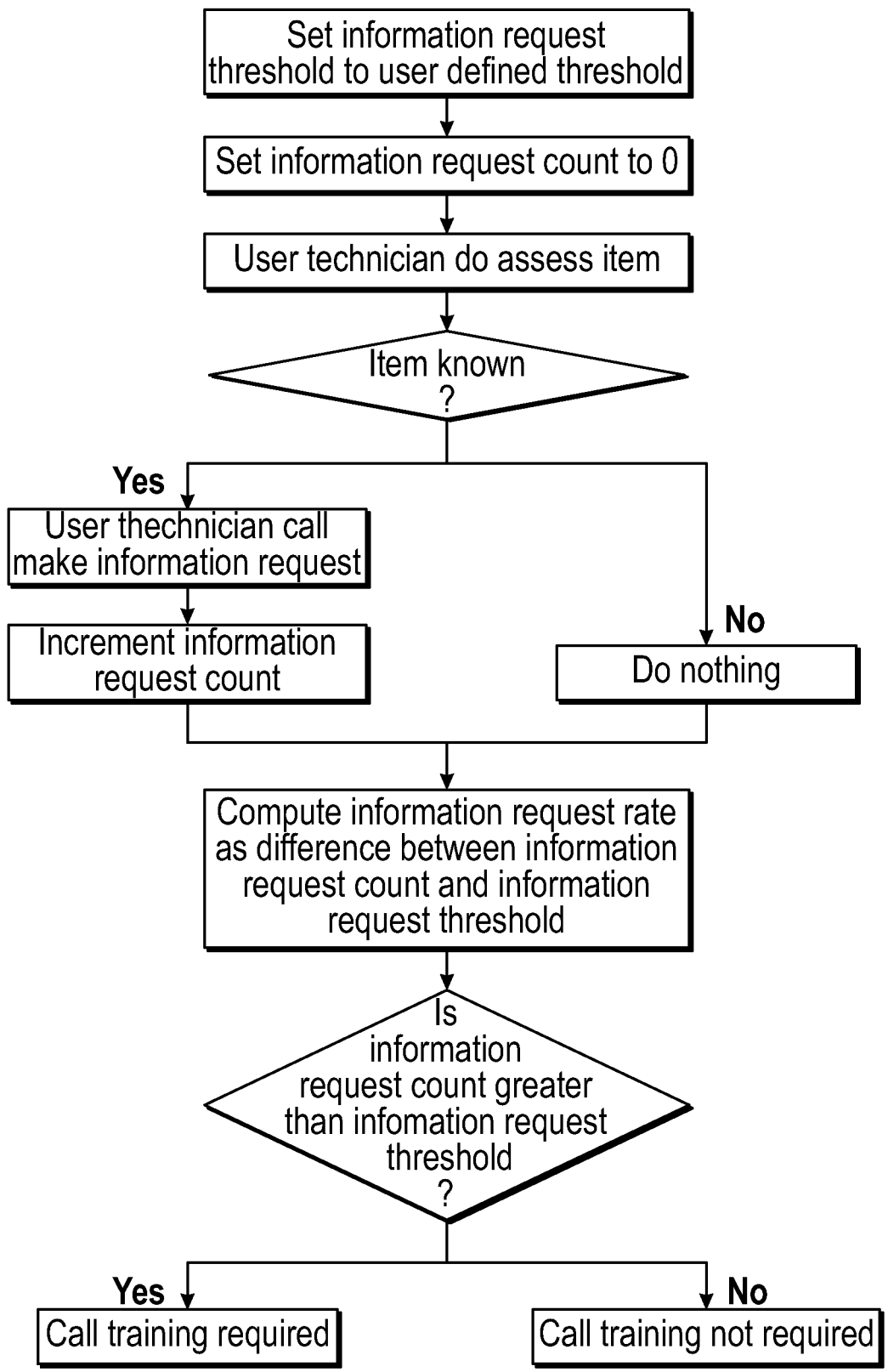
FIG. 15 illustrates a flowchart of a method of determining a training event, according to various embodiments.

In at least one embodiment, a profile can be developed for the user based on the record. The record associated with the technician also includes many information requests related to one or more surgical instruments as shown in FIG. 15. The record associated with the technician also includes a number of urgent requests from an operating room as shown in FIG.

Figure 17:
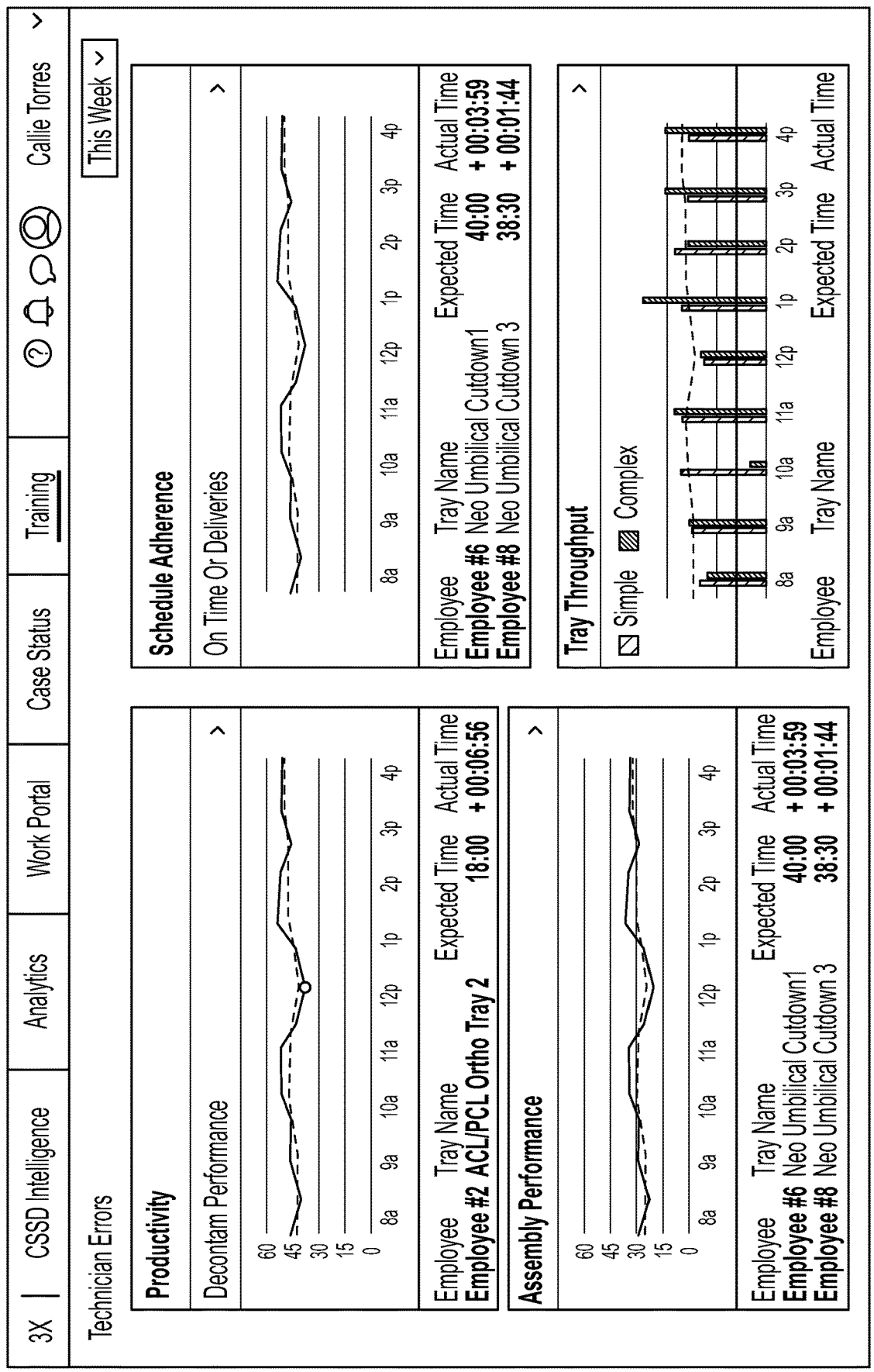
FIG. 17 illustrates a user interface featuring a technician management interface, according to various embodiments.

16, meaning that wrapped packages missing components (instruments or indicators) can be reflected on the technician's profile. The technician profile can be accessed using a management tool (shown in FIG. 17) that tracks performance metrics (e.g., the productivity, schedule adherence, assembly performance, and tray throughput) of an individual technician.

In block 370, the computing device can perform a record management operation which may include adding the surgical instrument to a group (e.g., when assembling pack) or removing the surgical instrument from the group (e.g., when disassembling a pack).

In block 380, the computing device can perform at least one operation in response to whether the surgical instrument is flagged. In addition to the operations described herein, the computing device can start tracking instrument time on the background surface, display cleaning instructions, send an alert to a second computing device (such as a manager smart phone) or from an operating room computer to a central sterile and supply department computer. In addition, the operation can include various personnel actions for the technician.

Figure 4:
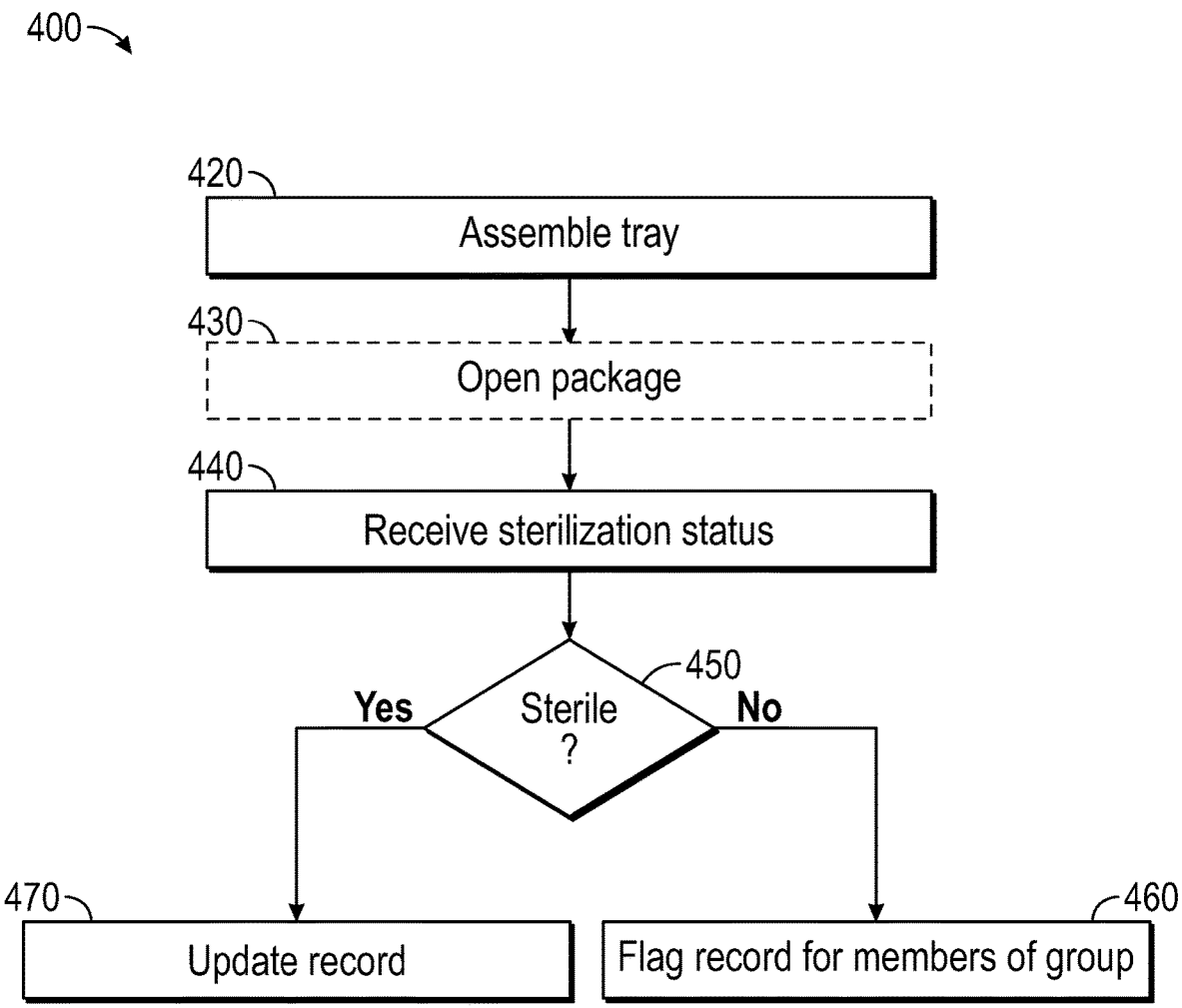
FIG. 4 illustrates a flowchart of a method of determining sterility of a wrapped package, according to various embodiments.

FIG. 4 illustrates a method 400 of using sterilization status to trigger a flag, according to various embodiments.

In block 420, a technician can assemble load assist device (e.g., tray) and the computing device can track the assembly of the load assist device. Block 420 can correspond to method 700 in FIG. 7.

Figure 7:
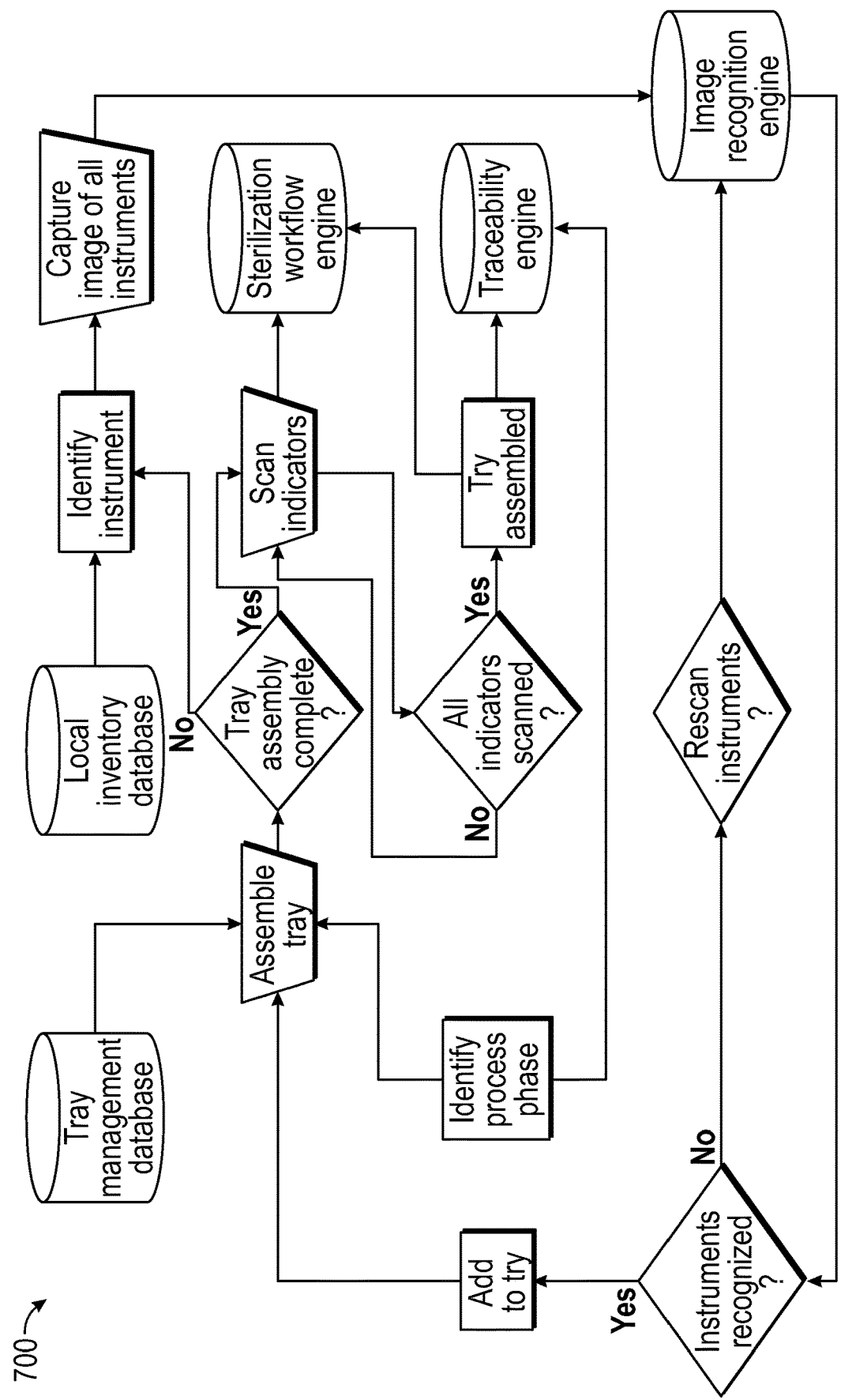
FIG. 7 illustrates a flowchart of a method of assembling a load assist device, according to various embodiments.

For example, in FIG. 7, uniquely identifiable trays with their uniquely identifiable instruments mapped accordingly in a system's LMDB and TMD, a user can be monitored for speed and accuracy at each step. Thresholds for speed and quality can be measured against and users who fail to meet those thresholds will be given personalized training through analysis of these data points through the AIE and TDE.

Trays can be assembled by properly identifying of those uniquely identifiable instruments to ensure trays are equipped with the required instruments. This is done through capturing an image of the instruments, which are then processed using an IRE. Properly identified instruments are then matched against the known tray to ensure they are proper for the tray. This process is repeated until all instruments required for the tray have been identified and assembled. Once assembled, the user must then scan the required chemical indicators (CI) and biological indicators (BI) needed to properly process the tray during the Sterilization phase. These steps are tracked in a Sterilization Workflow Engine (SWE) and Traceability Engine (TE), which are used to monitor the sterilization process and trace instruments and trays through that process. Those data points are their performance metrics are also forwarded for analysis by the AIE.

The computing device can determine, based on a machine vision technique from the image capture device, that a wrapped package is assembled with a group of one or more surgical instruments. The computing device can also determine whether a chemical indicator is present with the group using a machine vision technique. Exemplary machine vision techniques are discussed herein.

In block 430, the wrapped package can be opened to reveal contents. In at least one embodiment, the computing device can determine whether the wrapped package of the group is opened using the image capture device as discussed in copending application titled "Visual system for Status Detection of Wrapped Packages", which is incorporated by reference in its entirety.

In block 440, the computing device can receive a sterilization status for the group from the analytical device. In at least one embodiment, the analytical device can be an image capture device that is configured to determine a status of the indicator from an image. The analytical device can also be an ATP-based reader such as available under the trade designation Clean-Trace or a biological based reader such as available under the trade designation ATTEST.

In block 450, the computing device can perform at least one operation based on the sterilization status.

For example, in block 470, if the analytical device indicate sterility, then the record for group can indicate that the wrapped package was sterile and update each member of the group accordingly. In at least one embodiment, the computing device can update the record for the wrapped package to indicate the presence of the chemical indicator (independent of sterility).

In block 460, the computing device can associate a flag with a record in a datastore for the one or more surgical instruments in the group based on the sterilization status. This can indicate that each surgical instrument in the group was not sterile and trigger additional operations (such as user alerts or lockdown procedures).

Figure 8:
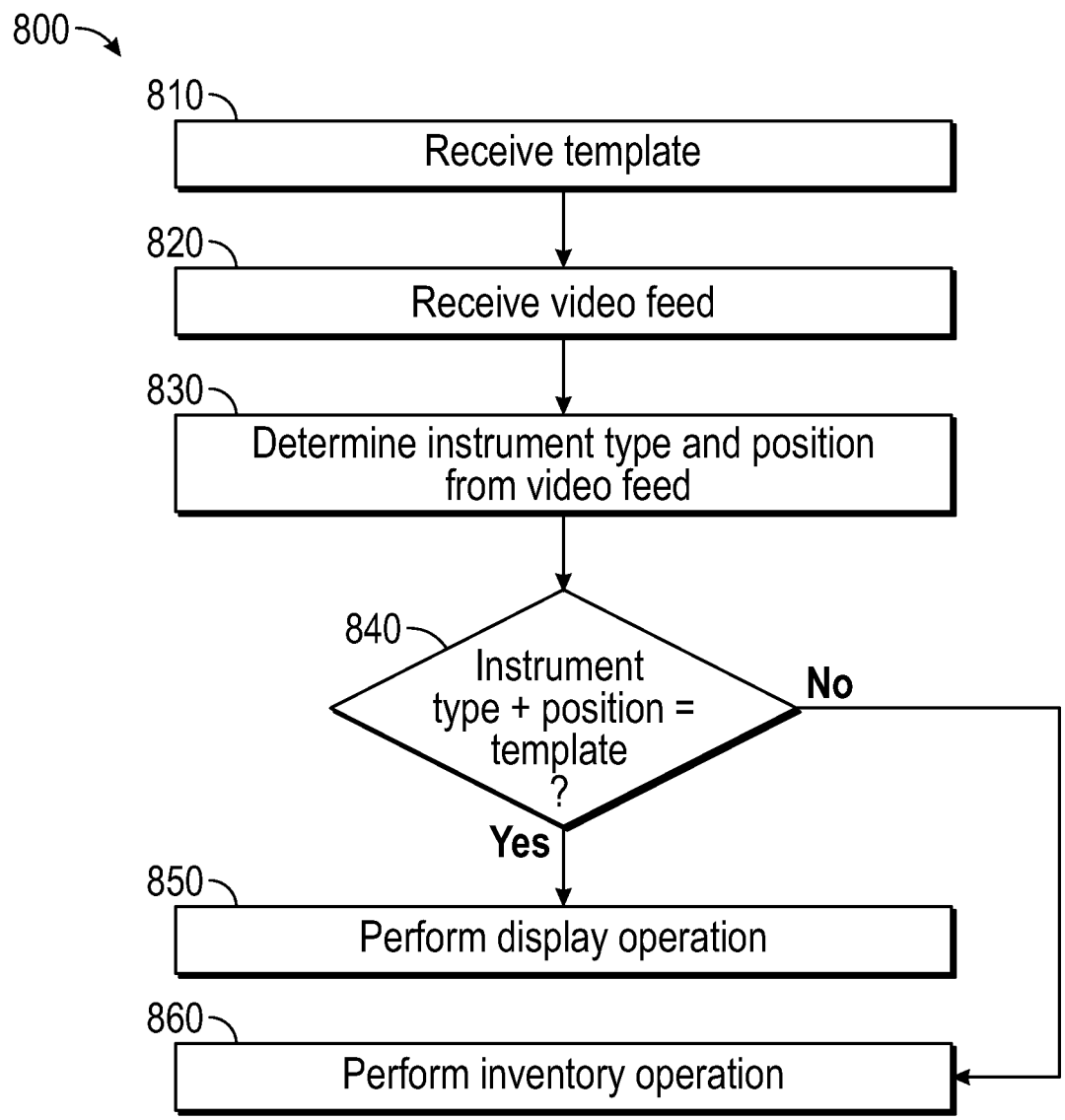
FIG. 8 illustrates a flowchart of a method of generating a template, according to various embodiments.

FIG. 8 illustrates a method 800 of interacting with a template, according to various embodiments.

In block 810, the computing device can receive a template for a plurality of surgical instruments, the template comprises an image describing position information for the plurality of surgical instruments. A template can be an orientation template that describes the position of each instrument relative to other instruments. The template can be based on common templates or wrapped package set ups found in the central sterile and supply department of a hospital. In at least one embodiment, the template is retrieved from a manufacturer. Custom templates can also be created by technicians and uploaded to the datastore.

In at least one embodiment, the template is fetched from the datastore and related to a group of one or more instruments. A wrapped package or load assist device can have an optically active article associated with the group of surgical instruments. In at least one embodiment, the article message can be read to trigger the retrieval of the template. For example, the computing device can receive the template based on data relating to the optically active article. In at least one embodiment, the optically active article is a retroreflective.

In block 820, the computing device can receive, from the image capture device, a video feed of the surgical instrument. In at least one embodiment, the surgical instrument is placed on a relatively planar surface by a technician such that it is visible to an image capture device. The planar surface can also include a background surface such as a scaled mat.

In block 830, the computing device can determine a type and position of the surgical instrument from the video feed as discussed using the machine vision techniques described herein. The video feed can also include a chemical indicator.

Figure 9:
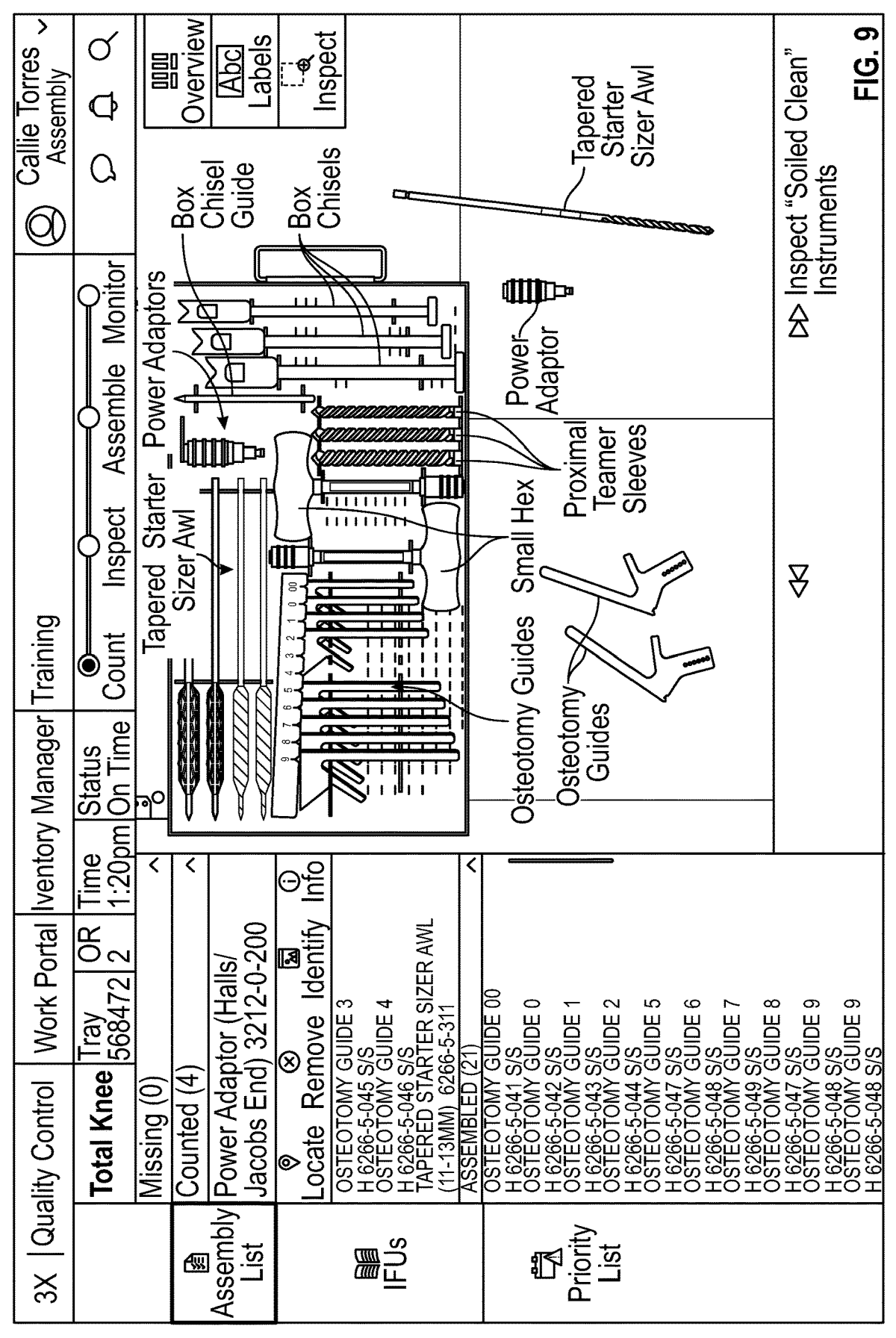
Figure 12:
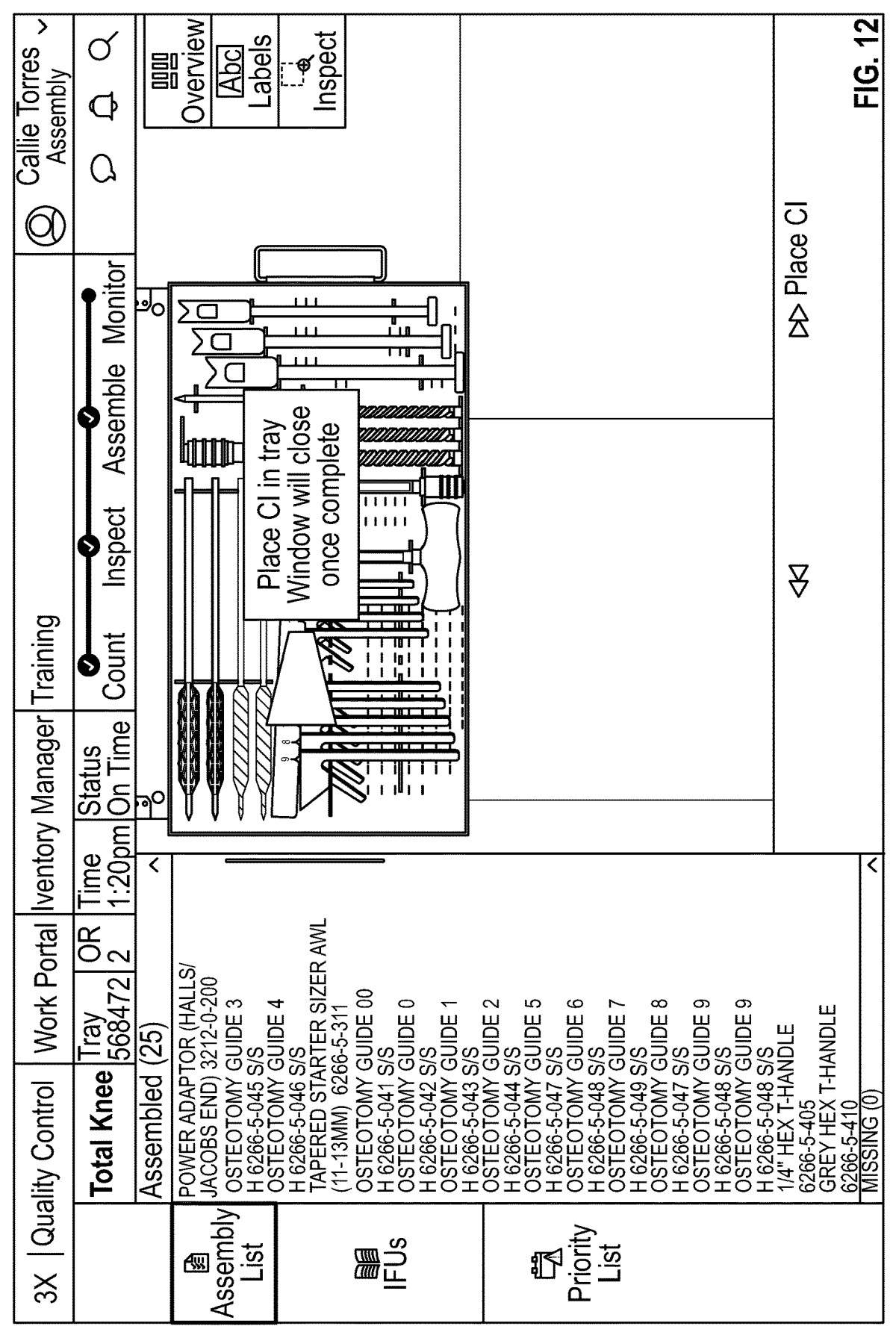

In block 840, the computing device can determine whether the type and position of the surgical instrument corresponds to a surgical instrument of the template. This can be based on the position of the surgical instrument relative to an expected location of the template. For example, FIG. 9 illustrates various locations where instruments are matched with the position in the template. FIG. 9 also illustrates that the tapered starter sizer awl is not in the correct position. In at least one embodiment, the positional information for a chemical indicator can be determined as well as shown on FIG. 12.

In response to the determination of the instrument type and position, the computing device can perform at least one operation. In block 850, the computing device can perform a display operation. In at least one embodiment, a display operation involves modification to the display or user interface.

For example, the computing device can display both the video feed of the surgical instrument and the template, the surgical instrument is superimposed over the template. The displaying can occur in real-time to allow a technician to adjust the position manually. In at least one embodiment, the computing device can change a color of a portion of the template corresponding to the surgical instrument based on a type and position of the surgical instrument relative to the template. For example, as shown in FIG. 10, as a surgical instrument is moved into position, the template region corresponding to the position of the instrument changes from red to green.

Figure 10:
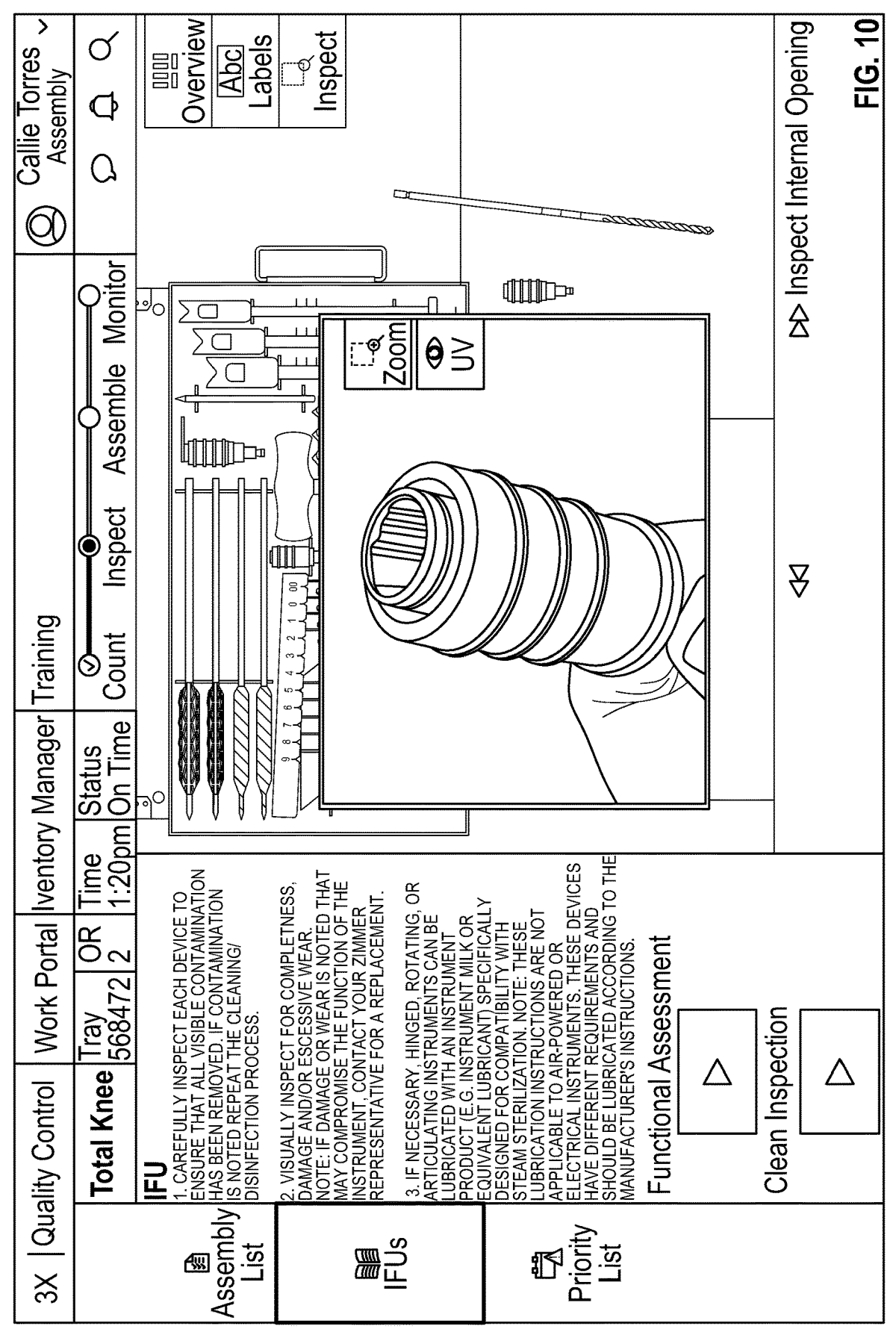

The computing device can also provide a zoomed video feed when the surgical instrument is proximate to an area defined by the template for the surgical instrument type as shown in FIG. 10. The zoomed video can access different functions of the image capture device (such as an optical zoom). In at least one embodiment, the zoomed video can be provided as a result of interaction with the user interface of the template (such as an icon to zoom).

Figure 11:
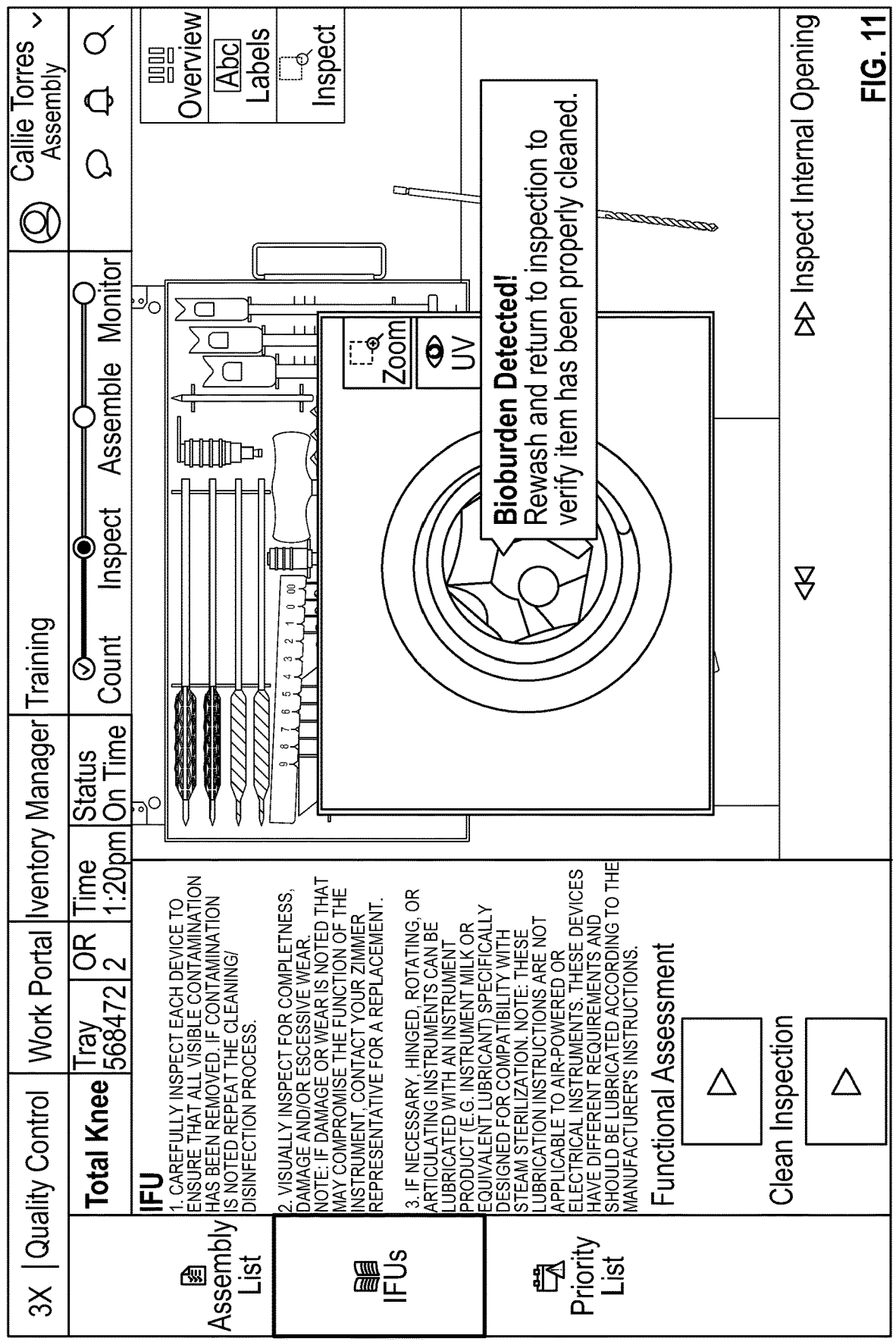
FIG. 11 illustrates an image of a user interface featuring a template with zoom capability and view selection, according to various embodiments.

The computing device can change views of the image capture device. For example, changing views can include various filters or even changing lighting conditions of the video feed. For example, the computing device can activate a light source (such as a UV light source) if an instrument is not in position. FIG. 11 shows an embodiment of the computing device activating a UV light source for an inspection mode to detect soil.

In block 860, the computing device can conduct an inventory operation. An inventory operation can include updating the record to reflect that the instrument is the right type and present but in the wrong position. Alternatively, if the instrument is not present, then the record can be updated to indicate that there is no presence of the instrument.

Various examples and implementations will be described in detail. These examples should not be construed as limiting the scope of the present disclosure in any manner, and changes and modifications may be made without departing from the spirit and scope of the disclosure. Further, only some end uses have been discussed herein, but end uses not specifically described herein are included within the scope of the present disclosure. As such, the scope of the present disclosure should be determined only by the claims.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor", as used may refer to any of the foregoing structure or any other structure suitable for implementation of the techniques described. In addition, in some respects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multithreaded processing, interrupt processing, or multiple processors, rather than sequentially.

In some examples, a computer-readable storage medium includes a non-transitory medium. The term "non-transitory" indicates, in some examples, that the storage medium is not embodied in a carrier wave or a propagated signal. In certain examples, a non-transitory storage medium stores data that can, over time, change (e.g., in RAM or cache).

Those having skill in the art will appreciate that many changes may be made to the details of the above-described examples and implementations without departing from the underlying principles thereof. The scope of the present disclosure should, therefore, be determined only by the following claims.

In some examples, an apparatus (e.g., an image capture device) or computing device comprises least one single core or multi core computer processing unit (CPU) and/or graphics processing unit (GPU). In some examples, the CPU is co-located with a camera, that is, disposed within proximity to the camera. In some examples, the CPU is mounted on the same board as the camera. In other examples, the CPU is not co-located with the camera and is connected to the camera by other means of communication, such as, for example, coaxial cables and/or wireless connections. In some examples, the CPU substantially concurrently processes multiple frames via operating system provided services, such as, for example, time slicing and scheduling. In other examples, the apparatus further comprises at least one multi-core CPU.

In some examples an apparatus or computing device produces bundles of data including, for example, date, time, images, barcode read data, Optical Character Recognition (OCR) read data, and other metadata, that may be useful in sterilization.

In some examples, pre-processing may increase the rate of processing images. In some examples, intelligent selection is performed via field-programmable gate array (FPGA) pre-processing which can process multiple channels at 50 fps. As an example, fifteen images may be processed by OCR from a first channel, but only three barcode images from a second channel may be processed during the same period. This difference in the number of images processed per channel may happen when one of the images (e.g., barcode image) is more complex.

The radiation detected by the camera can come from any of a number of sources. Of interest is the radiation reflected from the optically active article, and specifically, the amount of radiation reflected from each area inside that region of interest on the article. The camera or detection system collects radiation from each region of the optically active article with the goal of creating a difference (contrast) between the background and/or between each indicia or piece of identifying information on the optically active article. Contrast can be affected in numerous ways, including the use of coaxial radiation to overwhelm the amount of ambient radiation. The use of filters on the camera can help accentuate the differences between the indicia or identifying information and background by selectively removing undesired radiation wavelengths and passing only the desired radiation wavelengths.

List of Illustrative Embodiments

1. A system comprising:
   an image capture device;
   a computing device communicatively coupled to the image capture device, the computing device comprising one or more computer processors and a memory comprising instructions that when executed by the one or more computer processors cause the one or more computer processors to:
      receive a test image from the image capture device corresponding to a first surgical instrument;
      determine an identity type of the first surgical instrument using the test image in a machine vision technique;
      determining whether the first surgical instrument is flagged;
      perform at least one operation in response to whether the first surgical instrument is flagged.

2. The system of embodiment 1, wherein the computing device comprises a memory comprising instructions that when executed by the one or more computer processors cause the one or more computer processors to:
   adjust a confidence of the determination of the identity type based on an identity parameter.

3. The system of any of embodiments 1 or 2, further comprising:
   a datastore comprising one or more records for the first surgical instrument.

4. The system of embodiment 3, wherein the flag is derived from the one or more records from the datastore.

5. The system of any of embodiments 1 to 4, further comprising:
   a display communicatively coupled to the computing device.

6. The system of any of embodiments 4 to 5, wherein the first surgical instrument is flagged based on an economic status of the first surgical instrument,
   wherein the computing device comprises a memory comprising instructions that when executed by the one or more computer processors cause the one or more computer processors to:
      present, via the display, a visual indication of the economic status of the first surgical instrument.

7. The system of any of embodiments 1 to 3, wherein the first surgical instrument is flagged based on special handling instructions for the first surgical instrument:
   wherein to perform at least one operation the memory comprises instructions that when executed by the one or more computer processors cause the one or more computer processors to present the special handling instructions on the display.

8. The system of any of embodiments 1 to 7, wherein the first surgical instrument is flagged based on whether the first surgical instrument is missing from a group:
   wherein to perform at least one operation the memory comprises instructions that when executed by the one or more computer processors cause the one or more computer processors to present the group and a location associated with the group.

8a. The system of any of embodiments 1 to 7, wherein the first surgical instrument is flagged based on whether the first surgical instrument is broken or damaged;
   wherein to perform at least one operation the memory comprises instructions that when executed by the one or more computer processors cause the one or more computer processors to present an alert via a user interface.

8b. The system of any of embodiments 1 to 7, wherein the first surgical instrument is flagged based on whether an estimated processing time of the first surgical instrument is within a time threshold of an operating room schedule:
   wherein to perform at least one operation the memory comprises instructions that when executed by the one or more computer processors cause the one or more computer processors to present an alert via a user interface.

8c. The system of embodiment 8b, wherein the estimated processing time is based on real-time and historical device reprocessing data that is captured and analyzed by a machine vision technique.

9. The system of any of embodiments 1 to 8, wherein the first surgical instrument is flagged based on a record for the first surgical instrument not being present in the datastore:
wherein to perform at least one operation the memory comprises instructions that when executed by the one or more computer processors cause the one or more computer processors to perform a record management operation to the record for the first surgical instrument based on the determination of the identity type.

10. The system of embodiment 9, wherein the record management operation comprises adding the record to the datastore.

11. The system of embodiment 10, wherein the record management operation comprises adding details associated with the first surgical instrument manually.

12. The system of embodiment 11, wherein to determine the identity type of the first surgical instrument, the memory comprises instructions that when executed by the one or more computer processors cause the one or more computer processors to:
determine, with the image capture device, whether an article message is present on a surgical instrument; and
determine the identity type of the first surgical instrument using a machine vision technique based on whether the article message is present.

13. The system of embodiment 12, wherein the article message is a bar code, QR code, visual indication of an alphanumeric sequence, or combinations thereof.

14. The system of embodiment 13, wherein the bar code comprises color coded bar code stripes.

15. The system of embodiment 11 or 12, wherein to determine whether the article message is present occurs responsive to determining if a receipt or purchase order is available for the device; and if available, adding the receipt or purchase order to the record.

16. The system of any of embodiments 1 to 15, wherein whether the instrument is part of a wrapped package results in a flag;
wherein to perform at least one operation the memory comprises instructions that when executed by the one or more computer processors cause the one or more computer processors to determine whether a chemical indicator is present with the first surgical instrument using a machine vision technique;
wherein the record for the wrapped package is updated to indicate the presence of the chemical indicator.

17. The system of any of embodiments 1 to 16, wherein to perform at least one operation the memory comprises instructions that when executed by the one or more computer processors cause the one or more computer processors to track performance data of a technician.

18. The system of any of embodiments 1 to 17, wherein to perform at least one operation the memory comprises instructions that when executed by the one or more computer processors cause the one or more computer processors to update a record associated with a technician.

19. The system of embodiment 18, wherein the record associated with the technician also includes a number of information requests related to one or more surgical instruments.

20. The system of embodiment 19, wherein the record associated with the technician also includes a number of urgent requests from an operating room.

21. The system of any of embodiments 1 to 20, wherein a record for the first surgical instrument in the datastore is updated from a plurality of secondary sources.

22. The system of any of embodiments 1 to 21, wherein to determine the identity type, the memory comprises instructions that when executed by the one or more computer processors cause the one or more computer processors to:
receive a plurality of images corresponding to a plurality of surgical instruments comprising a first set of images that include surgical instruments having the instrument type;
generate a first set of feature values based on a visual representation of a surgical instrument in the image, wherein the first set of feature values correspond to features usable to determine an instrument type of the surgical instrument;
apply the first set of feature values for the first set of images to a first model to determine affiliation with a plurality of clusters based on shared features, wherein the first model does not use labels of the set of images;
assign an image from the first set of images to a cluster.

23. The system of embodiment 22, wherein one or more processors are configured to perform at least one operation based at least in part on the cluster assigned.

24. The system of embodiment 22, wherein one or more processors are configured to:
receive a second set of images corresponding to a first surgical instrument;
generate a second set of feature values from the second set of images;
apply the second set of feature values to a first plurality of models to determine the instrument type, each of the first plurality of models corresponds to a cluster from the plurality of clusters;
generate, based at least in part on the one or more processors processing the set of feature values with at least one model, an indication of the instrument type for the first surgical instrument; and
perform at least one operation based at least in part on the instrument type.

25. The system of embodiment 22, wherein at least one model from the first plurality of models is a supervised learning model executed by the one or more processors and the second set of feature values are input into the neural network.

26. The system of any of embodiments 20 to 25, wherein the memory comprises instructions that when executed by the one or more computer processors cause the one or more computer processors to:
apply a third set of feature values for a portion of the first set of images to a second model to determine affiliation with a plurality of subclusters for a cluster based on shared features, wherein the second model does not use labels of the set of images;
apply the second set of feature values to a second plurality of models to determine the instrument type, each of the second plurality of models corresponds to a subcluster from the plurality of subclusters.

27. The system of any of embodiments 20 to 26, wherein the memory comprises instructions that when executed by the one or more computer processors cause the one or more computer processors to: generate the indication of the instrument type based on ensemble modeling an output of each model of the plurality of models.

28. The system of any of embodiments 20 to 27, wherein the memory comprises instructions that when executed by the one or more computer processors cause the one or more computer processors to: transfer characteristics related to the second set of images between models of the first plurality of models and the first model.

29. The system of any of embodiments 20 to 28, wherein the first model is an unsupervised learning model.

30. The system of any of embodiments 20 to 29, wherein the first set of images is different than the second set of images.
31. The system of any of embodiments 20 to 30, wherein the neural network is a convolutional neural network.
32. The system of any of embodiments 20 to 31, wherein the unsupervised learning model implements a gaussian mixture model.
33. The system of any of embodiments 20 to 32, wherein the supervised learning model uses a Bayesian model.
34. The system of any of embodiments 20 to 33, wherein the supervised learning model uses at least one of logistic regression, random forest, support vector machine, or boosting.
35. The system of any of embodiments 20 to 34, wherein the first surgical instrument is disposed on a background surface;
wherein the memory comprises instructions that when executed by the one or more computer processors cause the one or more computer processors to receive the plurality of images from the image capture device, and pre-process an image of the plurality of images.
36. The system of embodiment 35, wherein, to pre-process the image, the memory comprises instructions that when executed by the one or more computer processors cause the one or more computer processors to:
receive an image of the first surgical instrument and the background surface from the image capture device;
generate a mask from the image by removing the background surface;
remove noise from the mask;
apply the mask to the image.
37. The system of embodiment 36, wherein to apply the mask, the memory comprises instructions that when executed by the one or more computer processors cause the one or more computer processors to align the mask with the feature.
38. The system of any of embodiments 35 to 37, further comprising:
a group of first surgical instruments wherein the background surface is an unwrapped sterilization pack; a chemical indicator proximate to the group of first surgical instruments;
wherein at least one of the features generated by the one or more processors is an indicator status of the chemical indicator and the second set of images comprises the chemical indicator.
39. The system of any of embodiments 36 to 38, wherein to generate a mask, the memory comprises instructions that when executed by the one or more computer processors cause the one or more computer processors to:
apply a background subtraction operation to the image;
modify one or more color channels of the image;
apply a morphological operator.
40. The system of any of embodiments 36 to 39, wherein to remove noise from mask, the memory comprises instructions that when executed by the one or more computer processors cause the one or more computer processors to:
extract a plurality of connected components from the image;
determine a first group of connected components that are smaller than a first threshold dimension;
determine a second group of connected components that are larger than a second threshold dimension;
remove a connected component from the first and second group that is within a threshold distance from an edge of the image.

41. The system of any of embodiments 22 to 40, wherein to receive the image corresponding to the first surgical instrument, the memory comprises instructions that when executed by the one or more computer processors cause the one or more computer processors to:
receive a masked image for the first surgical instrument from a datastore.
42. The system of any of embodiments 22 to 41, wherein to provide the plurality of images corresponding to the first surgical instrument, the memory comprises instructions that when executed by the one or more computer processors cause the one or more computer processors to:
select the first surgical instrument based on an instrument attribute.
43. A system comprising:
an image capture device;
an analytical device;
a computing device communicatively coupled to the image capture device and the analytical device, the computing device comprising one or more computer processors and a memory comprising instructions that when executed by the one or more computer processors cause the one or more computer processors to:
determine, based on a machine vision technique from the image capture device, that a wrapped package is assembled with a group of one or more surgical instruments;
receive a sterilization status for the group from the analytical device;
perform at least one operation based on the sterilization status.
44. The system of embodiment 43, wherein to perform at least one operation the memory comprises instructions that when executed by the one or more computer processors cause the one or more computer processors to flag a record in a datastore for the one or more surgical instruments in the group based on the sterilization status.
45. The system of embodiment 43 or 44, wherein the memory comprises instructions that when executed by the one or more computer processors cause the one or more computer processors to determine whether the wrapped package of the group is opened using the image capture device.
46. The system of any of embodiments 43 to 45, wherein, to determine that a wrapped package is assembled, the memory comprises instructions that when executed by the one or more computer processors cause the one or more computer processors to determine whether a chemical indicator is present with the group using a machine vision technique;
wherein performing the at least one operation comprises updating the record for the wrapped package to indicate the presence of the chemical indicator.
47. The system of any of embodiments 43 to 46, wherein to determine that a wrapped package is assembled, the memory comprises instructions that when executed by the one or more computer processors cause the one or more computer processors to determine whether a surgical instrument and a chemical indicator are present.
48. The system of embodiment 47, wherein to determine whether a surgical instrument and chemical indicator are present, the memory comprises instructions that when executed by the one or more computer processors cause the one or more computer processors to:
receive an image corresponding to a surgical instrument and a chemical indicator;
generate a set of feature values based on a visual representation of the first surgical instrument in the image, wherein the set of feature values correspond to features usable to determine an instrument type of the surgical instrument, wherein at least one of the set of feature values is the chemical indicator;

apply the set of feature values to at least one model that is trained based at least in part on a set of images that include surgical instruments having the instrument type, to determine the instrument type and the chemical indicator; and performing at least one operation based at least in part on the instrument type and the chemical indicator.

49. The system of embodiment 48, wherein the memory comprises instructions that when executed by the one or more computer processors cause the one or more computer processors to:

pre-process the image responsive to receiving the image.

50. The system of embodiment 49, further comprising a background surface.

51. The system of any of embodiments 48 or 50, wherein to pre-process the image, the memory comprises instructions that when executed by the one or more computer processors cause the one or more computer processors to:

receive the image of the instrument and a background surface from the image capture device;

generate a mask from the image by removing the background surface;

remove noise from the mask;

apply the mask to the image.

52. The system of embodiment 51, wherein to apply the mask, the memory comprises instructions that when executed by the one or more computer processors cause the one or more computer processors to align the mask with the feature.

53. The system of embodiment 51, wherein to generate a mask, the memory comprises instructions that when executed by the one or more computer processors cause the one or more computer processors to:

apply a background subtraction to the image;

modify color channels of the image;

apply a morphological operator.

54. The system of embodiment 51, wherein to remove noise from mask the memory comprises instructions that when executed by the one or more computer processors cause the one or more computer processors to:

extract a plurality of connected components from the image;

determine a first group of connected components that are smaller than a first threshold dimension;

determine a second group of connected components that are larger than a second threshold dimension;

remove a connected component from the first and second group that is within a threshold distance from an edge of the image.

55. The system of embodiment 54, wherein applying the set of feature values to at least one model comprises:

identifying an instrument feature of the surgical instrument relative to a plurality of instrument features from a plurality of instruments;

determining an instrument type based on a comparison with the plurality of instrument features for a subset of the plurality of instruments.

56. The system of embodiment 55, wherein the instrument feature comprises at least one of the length, width, length/width ratio, area, perimeter, histogram of oriented gradients feature, or Gabor-like features of a connected component.

57. The system of any of embodiments 47 to 56, wherein the at least one model includes a supervised machine learning model.

58. The system of any of embodiments 47 to 57, wherein to determine an instrument type, the memory comprises instructions that when executed by the one or more computer processors cause the one or more computer processors to:

receive a test image of a plurality of instruments and the background surface from the image capture device;

apply the mask for a first surgical instrument to the test image;

apply a pattern matching model to an image for the first surgical instrument relative and the masked test image;

determine that the masked test image is matches the instrument type as the first surgical instrument based on the pattern matching model.

59. The system of embodiment 58, wherein to apply a pattern matching model, the memory comprises instructions that when executed by the one or more computer processors cause the one or more computer processors to:

extract keypoints from the masked test image;

determine the keypoints that match between the masked test image and an image for the first surgical instrument;

determine that the first surgical instrument is present based on a quantity of matched keypoints.

60. The system of embodiment 58, wherein the memory comprises instructions that when executed by the one or more computer processors cause the one or more computer processors to determine that the first surgical instrument is present based on a score associated with matching pairs of keypoints.

61. A system comprising:

an image capture device:

a surgical instrument;

a display;

a computing device communicatively coupled to the image capture device, the computing device comprising one or more computer processors and a memory comprising instructions that when executed by the one or more computer processors cause the one or more computer processors to:

receive a template for a plurality of surgical instruments, the template comprises an image describing position information for the plurality of surgical instruments;

receive, from the image capture device, a video feed of the surgical instrument;

determine a type and position of the surgical instrument from the video feed;

determine whether the type and position of the surgical instrument corresponds to a surgical instrument of the template:

perform at least one operation in response to the determination of the identity of the one or more surgical instruments.

62. The system of embodiment 61, wherein the memory comprises instructions that when executed by the one or more computer processors cause the one or more computer processors to:

display both the video feed of the surgical instrument and the template, the surgical instrument is superimposed over the template.

63. The system of embodiment 62, wherein the at least one operation comprises providing a zoomed video feed when the surgical instrument is proximate to an area defined by the template for the surgical instrument type.

64. The system of embodiment 61 or 62, wherein the at least one operation comprises changing a color of a portion of the template corresponding to the surgical instrument based on a type and position of the surgical instrument relative to the template.

65. The system of any of embodiments 61 to 63, wherein receiving the template for a plurality of surgical instruments comprises reading an optically active article on the package;
receiving the template based on data relating to the optically active article.
66. The system of embodiment 65, wherein the optically active article is a retroreflective.
67. The system of embodiment 61, further comprising a planar surface, wherein the surgical instrument is placed on the planar surface.
68. The system of any of embodiments 61 to 67, wherein the at least one operation is modifying a record for the first surgical instrument on a datastore based at least in part on the instrument type of the first surgical instrument.
68a. The system of any of embodiments 61 to 67, wherein the memory comprises instructions that when executed by the one or more computer processors cause the one or more computer processors to: dispense pre-cleaning solution by evaluated color of a chemical solution to determine proper dilution level for the first surgical instrument.
69. The system of embodiments 1 to 54 or system of embodiments 55 to 68, comprising a datastore, wherein the modifying the record comprises at least one of adding a record, changing a record, or deleting a record in response to determining the instrument type.
70. The system of embodiment 69, wherein adding a record occurs responsive to the first surgical instrument not being present on the datastore.
71. The system of embodiment 70, wherein the first surgical instrument is not present during an instrument check in process.
72. The system of embodiment 69, wherein the one or more processors is configured to associate at least one image of the first surgical instrument with the record.
73. The system of any of embodiments 72, wherein the one or more processors is configured to associate the record of the first surgical instrument with a plurality of instruments in a group.
74. The system of any of embodiments 69 to 73, wherein the datastore comprises technician cleaning instructions associated with a record for the first surgical instrument.
75. The system of embodiment 74, wherein the technician cleaning instructions comprises a video.
76. The system of embodiment 74 or 75, wherein the datastore comprises a plurality of time milestones based on the technician cleaning instructions associated with the record for the first surgical instrument.
77. The system of any of embodiments 69 to 76, further comprising a display, wherein the display is configured to display at least some data associated with the record.
78. The system of embodiment 76, wherein the one or more processors are configured to capture a video feed from the image capture device and determine whether at least one of the plurality of time milestones is met.
79. The system of any of embodiments 69 to 78, wherein the operation of the one or more processors comprises accessing the record from the datastore and determine based on the image received from the image capture device whether a second surgical instrument is present.
80. The system of embodiment 79, wherein the operation is to alert a user if the second surgical instrument is not present.
81. The system of any of embodiments 69 to 76, further comprising a quantitative biological tester that provides an indication of biological activity of a surface.
82. The system of embodiment 81, wherein the quantitative biological tester determines the indication from the first instrument and provides the indication to the datastore so that the indication is associated with the record.
83. The system of any of embodiments 69 to 82, wherein the one or more processors are configured to determine a prioritization for a group of instruments based on the record.
84. The system of any of embodiments 69 to 83, wherein the one or more processors are configured to determine a group of surgical instruments in a pack from a plurality of records, and determining the surgical instruments not present based on the based on the second set of images.
85. A computer-implemented method comprising:
receive a test image, from the image capture device, corresponding to a first surgical instrument;
determine an identity type of the first surgical instrument using the test image in a machine vision technique;
determining whether the first surgical instrument is flagged;
perform at least one operation in response to whether the first surgical instrument is flagged.
86. The method of embodiment 85, further comprising:
adjusting a confidence of the determination of the identity type based on an identity parameter.
87. The method of embodiment 85 or 86, wherein the flag is derived from the one or more records from the datastore.
88. The method of any of embodiments 85 to 87, further comprising:
presenting, via a display, a visual indication of the economic status of the first surgical instrument:
wherein the first surgical instrument is flagged based on an economic status of the first surgical instrument.
89. The method of any of embodiments 85 to 88, wherein the first surgical instrument is flagged based on special handling instructions for the first surgical instrument;
wherein performing at least one operation comprises presenting the special handling instructions on the display.
90. The method of any of embodiments 85 to 89, wherein the first surgical instrument is flagged based on whether the first surgical instrument is missing from a group;
wherein performing at least one operation comprises presenting the group and a location associated with the group.
91. The method of any of embodiments 85 to 90, wherein the first surgical instrument is flagged based on a record for the first surgical instrument not being present in the datastore;
wherein performing at least one operation comprises performing a record management operation to the record for the first surgical instrument based on the determination of the identity type.
92. The method of embodiment 91, wherein the record management operation comprises adding the record to the datastore.
93. The method of embodiment 92, wherein the record management operation comprises adding details associated with the first surgical instrument manually.
94. The method of embodiment 93, wherein determining the identity type of the first surgical instrument comprises:
determining, with the image capture device, whether an article message is present on a surgical instrument; and
determining the identity type of the first surgical instrument using a machine vision technique based on whether the article message is present.
95. The method of embodiment 94, wherein the article message is a bar code, QR code, visual indication of an alphanumeric sequence, or combinations thereof.
96. The method of embodiment 95, wherein the bar code comprises color coded bar code stripes.

97. The method of any of embodiments 94 to 96, wherein determining whether the article message is present occurs responsive to determining if a receipt or purchase order is available for the device, and if available, adding the receipt or purchase order to the record.

98. A computer-implemented method, comprising:
determining, based on a machine vision technique from the image capture device, that a wrapped package is assembled with a group of one or more surgical instruments;
receiving a sterilization status for the group from an analytical device;
performing at least one operation based on the sterilization status.

99. The method of embodiment 98, wherein performing at least one operation comprises flagging a record in a datastore for the one or more surgical instruments in the group based on the sterilization status.

100. A computer implemented method comprising:
receiving a template for a plurality of surgical instruments, the template comprises an image describing position information for the plurality of surgical instruments:
receiving, from the image capture device, a video feed of the surgical instrument:
determining a type and position of the surgical instrument from the video feed:
determining whether the type and position of the surgical instrument corresponds to a surgical instrument of the template:
performing at least one operation in response to the determination of the identity of the one or more surgical instruments.

101. The method of embodiment 100, further comprising: displaying both the video feed of the surgical instrument and the template, the surgical instrument is superimposed over the template.

102. The method of embodiment 100, wherein performing the at least one operation comprises providing a zoomed video feed when the surgical instrument is proximate to an area defined by the template for the surgical instrument type.

What is claimed is:

1. A system comprising:
an image capture device;
a computing device communicatively coupled to the image capture device, the computing device comprising one or more computer processors and a memory comprising instructions that when executed by the one or more computer processors cause the one or more computer processors to:
receive a test image from the image capture device corresponding to a first surgical instrument;
determine an identity type of the first surgical instrument using the test image in a machine vision technique by:
receiving a plurality of images corresponding to a plurality of surgical instruments comprising a first set of images that include surgical instruments having the identity type;
generating a first set of feature values based on a visual representation of a surgical instrument from the plurality of surgical images in an image from the plurality of images, wherein the first set of feature values correspond to features usable to determine the identity type of the surgical instrument from the plurality of surgical images;
applying the first set of feature values for the first set of images to a first model to determine affiliation with a plurality of clusters based on shared features of the first set of images;
assigning the test image to a cluster from the plurality of clusters based on affiliation, wherein the cluster is associated with the identity type;
determine whether the first surgical instrument is flagged; and
perform at least one operation in response to whether the first surgical instrument is flagged.

2. The system of claim 1, wherein the computing device comprises a memory comprising instructions that when executed by the one or more computer processors cause the one or more computer processors to:
adjust a confidence of the determination of the identity type based on an identity parameter.

3. The system of claim 1, further comprising:
a datastore comprising one or more records for the first surgical instrument.

4. The system of claim 3, wherein a flag is derived from the one or more records from the datastore.

5. The system of claim 3, wherein the first surgical instrument is flagged based on a record for the first surgical instrument not being present in the datastore;
wherein to perform at least one operation the memory comprises instructions that when executed by the one or more computer processors cause the one or more computer processors to perform a record management operation to the record for the first surgical instrument based on the determination of the identity type, wherein the record management operation comprises adding the record to the datastore.

6. The system of claim 5, wherein the record management operation comprises adding details associated with the first surgical instrument manually.

7. The system of claim 6, wherein to determine the identity type of the first surgical instrument, the memory comprises instructions that when executed by the one or more computer processors cause the one or more computer processors to:
determine, with the image capture device, whether an article message is present on a surgical instrument; and
determine the identity type of the first surgical instrument using a machine vision technique based on whether the article message is present.

8. The system of claim 7, wherein the article message is a bar code, QR code, visual indication of an alphanumeric sequence, or combinations thereof.

9. The system of claim 8, wherein the bar code comprises color coded bar code stripes.

10. The system of claim 7, wherein to determine whether the article message is present occurs responsive to determining if a receipt or purchase order is available for the device; and
if available, adding the receipt or purchase order to the record.

11. The system of claim 1, further comprising:
a display communicatively coupled to the computing device.

12. The system of claim 11, wherein the first surgical instrument is flagged based on an economic status of the first surgical instrument,
wherein the computing device comprises a memory comprising instructions that when executed by the one or more computer processors cause the one or more computer processors to:
present, via the display, a visual indication of the economic status of the first surgical instrument.

13. The system of claim 11, wherein the first surgical instrument is flagged based on special handling instructions for the first surgical instrument;
wherein to perform at least one operation the memory comprises instructions that when executed by the one or more computer processors cause the one or more computer processors to present the special handling instructions on the display.

14. The system of claim 11, wherein the first surgical instrument is flagged based on whether the first surgical instrument is missing from a group;
wherein to perform at least one operation the memory comprises instructions that when executed by the one or more computer processors cause the one or more computer processors to present the group and a location associated with the group.

15. A system comprising:
an image capture device;
an analytical device;
a computing device communicatively coupled to the image capture device and the analytical device, the computing device comprising one or more computer processors and a memory comprising instructions that when executed by the one or more computer processors cause the one or more computer processors to:
determine, based on a machine vision technique from the image capture device, that a wrapped package is assembled with a group of one or more surgical instruments by:
receiving an image of a surgical instrument and a background surface from the image capture device,
pre-processing the image responsive to receiving the image, further comprising:
generating a mask from the image by removing the background surface;
removing noise from the mask, and
applying the mask to the image,
receive a sterilization status for the group from the analytical device; and
perform at least one operation based on the sterilization status.

16. The system of claim 15, wherein to perform at least one operation the memory comprises instructions that when executed by the one or more computer processors cause the one or more computer processors to flag a record in a datastore for the one or more surgical instruments in the group based on the sterilization status.

17. The system of claim 15, wherein to apply the mask, the memory comprises instructions that when executed by the one or more computer processors cause the one or more computer processors to align the mask with a feature.

18. The system of claim 15, wherein to generate a mask, the memory comprises instructions that when executed by the one or more computer processors cause the one or more computer processors to:
apply a background subtraction to the image;
modify color channels of the image;
apply a morphological operator.

19. The system of claim 15, wherein to remove noise from mask the memory comprises instructions that when executed by the one or more computer processors cause the one or more computer processors to:
extract a plurality of connected components from the image;
determine a first group of connected components that are smaller than a first threshold dimension; determine a second group of connected components that are larger than a second threshold dimension; and
remove a connected component from the first and second group that is within a threshold distance from an edge of the image.

20. A system comprising:
an image capture device;
a surgical instrument;
a display;
a computing device communicatively coupled to the image capture device, the computing device comprising one or more computer processors and a memory comprising instructions that when executed by the one or more computer processors cause the one or more computer processors to:
receive a template for a plurality of surgical instruments, the template comprises an image describing position information for the plurality of surgical instruments;
receive, from the image capture device, a video feed of the surgical instrument;
determine an instrument type and position of the surgical instrument from the video feed;
determine whether the type and position of the surgical instrument corresponds to a surgical instrument of the template;
perform at least one operation in response to the determination of the instrument type of the surgical instrument, wherein the at least one operation comprises providing a zoomed video feed when the surgical instrument is proximate to an area defined by the template for the surgical instrument type.

21. The system of claim 20, wherein the memory comprises instructions that when executed by the one or more computer processors cause the one or more computer processors to:
display both the video feed of the surgical instrument and the template, the surgical instrument is superimposed over the template.

* * * * *

UNITED STATES PATENT AND TRADEMARK OFFICE
CERTIFICATE OF CORRECTION

Page 1 of 2

PATENT NO. : 10,874,759 B2
APPLICATION NO. : 16/359552
DATED : December 29, 2020
INVENTOR(S) : Ma et al.

It is certified that error appears in the above-identified patent and that said Letters Patent is hereby corrected as shown below:

In the Drawings

<u>Drawing Sheet 3 of 19 (Reference Numeral 320) (FIG. 3)</u>
Line 1, Delete "identiy" and insert -- identity --, therefor.

<u>Drawing Sheet 10 of 19 (FIG. 10)</u>
Line 11 (Approx.), Delete "COMPLETNESS," and insert -- COMPLETENESS, --, therefor.

<u>Drawing Sheet 11 of 19 (FIG. 11)</u>
Line 11 (Approx.), Delete "COMPLETNESS," and insert -- COMPLETENESS, --, therefor.

<u>Drawing Sheet 15 of 19 (FIG. 15)</u>
Line 8 (Approx.), Delete "thechnician" and insert -- technician --, therefor.

<u>Drawing Sheet 15 of 19 (FIG. 15)</u>
Line 20 (Approx.), Delete "infomation" and insert -- information --, therefor.

<u>Drawing Sheet 19 of 19 (FIG. 19)</u>
Line 24 (Approx.), Delete "Scalples" and insert -- Scalpels --, therefor.
Line 39 (Approx.), Delete "snicky" and insert -- sticky --, therefor.
Line 40 (Approx.), Delete "water proof" and insert -- waterproof --, therefor.
Line 42 (Approx.), Delete "may dypes" and insert -- tray types --, therefor.

In the Specification

<u>Column 3</u>
Line 46, Delete "increased," and insert -- increased --, therefor.

<u>Column 13</u>
Line 16, Delete "129" and insert -- 129. --, therefor.

Signed and Sealed this
Twenty-sixth Day of October, 2021

Drew Hirshfeld
*Performing the Functions and Duties of the
Under Secretary of Commerce for Intellectual Property and
Director of the United States Patent and Trademark Office*

Column 22
Line 35, Delete "instrument:" and insert -- instrument; --, therefor.
Line 43, Delete "group:" and insert -- group; --, therefor.
Line 59, Delete "schedule:" and insert -- schedule; --, therefor.

Column 23
Line 3, Delete "datastore:" and insert -- datastore; --, therefor.

Column 28
Line 30, Delete "device:" and insert -- device; --, therefor.
Lines 47-48, Delete "template:" and insert -- template; --, therefor.

Column 30
Line 29, Delete "instrument:" and insert -- instrument; --, therefor.

Column 31
Line 4, Delete "device," and insert -- device; --, therefor.
Line 21, Delete "instruments:" and insert -- instruments; --, therefor.
Line 23, Delete "instrument:" and insert -- instrument; --, therefor.
Line 25, Delete "feed:" and insert -- feed; --, therefor.
Lines 27-28, Delete "template:" and insert -- template; --, therefor.